United States Patent [19]

Mihayashi et al.

[11] Patent Number: 5,476,759
[45] Date of Patent: * Dec. 19, 1995

[54] SILVER HALIDE COLOR PHOTOGRAPHIC MATERIAL

[75] Inventors: Keiji Mihayashi; Seiji Ichijima; Toshio Kawagishi; Naoki Saito; Masuji Motoki, all of Kanagawa, Japan

[73] Assignee: Fuji Photo Film Co., Ltd., Kanagawa, Japan

[ * ] Notice: The portion of the term of this patent subsequent to Mar. 16, 2010, has been disclaimed.

[21] Appl. No.: 103,045

[22] Filed: Jul. 28, 1993

Related U.S. Application Data

[63] Continuation-in-part of Ser. No. 667,806, Mar. 11, 1991, abandoned.

[30] Foreign Application Priority Data

Mar. 12, 1990 [JP] Japan ................................ 2-60735

[51] Int. Cl.$^6$ .................................... G03C 1/46
[52] U.S. Cl. ..................... 430/505; 430/544; 430/567; 430/506; 430/550; 430/558; 430/957; 430/548; 430/551
[58] Field of Search .................... 430/505, 544, 430/567, 506, 550, 558, 957, 548, 551, 548

[56] References Cited

U.S. PATENT DOCUMENTS

| | | | |
|---|---|---|---|
| 4,477,563 | 10/1984 | Ichijima et al. | 430/544 |
| 5,085,979 | 2/1992 | Yamagami et al. | 430/505 |
| 5,126,236 | 6/1992 | Mihayashi et al. | 430/505 |
| 5,194,369 | 3/1993 | Mihayashi et al. | 430/544 |
| 5,215,872 | 6/1993 | Goto et al. | 430/957 |

FOREIGN PATENT DOCUMENTS

| | | | |
|---|---|---|---|
| 0233641 | 8/1987 | European Pat. Off. | 430/957 |
| 0337370 | 10/1989 | European Pat. Off. | |
| 3209486 | 9/1982 | Germany | |

*Primary Examiner*—Thomas R. Neville
*Attorney, Agent, or Firm*—Birch, Stewart, Kolasch & Birch

[57] ABSTRACT

A silver halide color photographic material comprising a support having thereon at least one light-sensitive silver halide emulsion layer is disclosed, wherein said light-sensitive material contains a DIR coupler represented by formula (I):

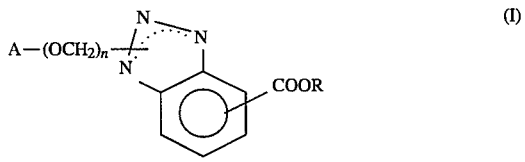

wherein A represents a coupler residue; R represents an alkyl group having from 1 to 4 carbon atoms or a pyridyl group; and n represents 1 when A represents a phenol type or naphthol type coupler residue, or n represents 0 when A represents other coupler residues, and said emulsion layer contains chemically sensitized silver halide grains which individually have a distinct layer comprising silver iodobromide containing from 7 to 45 mol % of silver iodide and which individually have an overall silver iodide content of more than 4 mol %. The photographic material is excellent in sensitivity, graininess, sharpness, color reproducibility, and preservability and is less liable to variation in photographic performance properties even when continuously processed under replenishment.

19 Claims, No Drawings

SILVER HALIDE COLOR PHOTOGRAPHIC MATERIAL

This application is a continuation in part of application Ser. No. 07/667,806, filed 03/11/91, now abandoned.

FIELD OF THE INVENTION

This invention relates to a silver halide color photographic material and, more particularly, to a silver halide color photographic material essentially containing (1) a silver halide emulsion comprising silver halide grains locally having a high silver iodide content and (2) a DIR coupler capable of releasing a development inhibitor which, after being released into a developing solution, is converted to a substance having no substantial influences on photographic performance properties.

BACKGROUND OF THE INVENTION

There has been a demand for a silver halide light-sensitive material particularly for shooting which achieves high sensitivity, such as ISO 400 sensitivity (Super HG-400), while exhibiting excellent image quality, including graininess, sharpness and color reproducibility, equal to that of light-sensitive materials having ISO sensitivity 100.

As a means for improving graininess, silver halide grains having a distinct stratiform structure containing from 7 to 45 mol % of silver iodide and having an average silver iodide content of at least 7 mol % have been proposed as disclosed in JP-A-60-143331 (the term "JP-A" as used herein means an "unexamined published Japanese patent application"). Since a mere use of such silver halide grains still leaves problems of sharpness and color reproducibility, it has been recently proposed to use these emulsion grains in combination with a so-called DIR coupler capable of imagewise releasing a development inhibitor as disclosed in JP-A-1-186938, JP-A- 1-259359, JP-A-1-269935, and JP-A-2-28637. These techniques brought about some improvements in graininess, sharpness, and color reproducibility, but the reached level was still unsatisfactory. In addition, when light-sensitive materials having the above-described means are processed in a usual manner currently spread in photofinishing laboratories, i.e., continuously processed while supplying a developing solution for replenishment, it turned out that a developing solution gradually comes to have decreased or increased activity.

On the other hand, hydrolyzable DIR couplers or compounds which improve sharpness as well as color reproducibility while causing no change in activity of a developing solution have been proposed as described in JP-A-57-151944, JP-A-58-205150, JP-A-1-280755, and U.S. Pat. No. 4,782,012. These DIR couplers or compounds are capable of releasing a development inhibitor moiety which undergoes hydrolysis in a developing solution to lose its inhibitory activity. While variations of activity of a developing solution were somewhat suppressed by using these compounds, the produced effects were still insufficient. In particular, when those capable of releasing a development inhibitor which releases an aryloxy ion or an arylamine ion when inactivated in a developing solution are used, it was found that the released aryloxy ion or an arylamine ion is incorporated into oil droplets of couplers of a light-sensitive material, causing variations in coupling activity of compounds. Further, so-called timing type DIR couplers need improvements in stability and cost for synthesis. Furthermore, DIR couplers which release a development inhibitor via a sulfur atom thereof as described in U.S. Pat. No. 4,782,012 have low coupling activity, i.e., low rate of development inhibitor release so that sufficient improved effects on color reproducibility and sharpness can not be obtained.

SUMMARY OF THE INVENTION

An object of the present invention is to provide a light-sensitive material which satisfies sensitivity, graininess, sharpness, color reproducibility, and preservability.

Another object of the present invention is to provide a light-sensitive material which undergoes extremely reduced variations in photographic performance properties even when processed continuously while replenishing a developing solution.

A further object of the present invention is to provide a light-sensitive material containing a DIR coupler which can be synthesized through a short route at a low cost and which has excellent stability and high coupling activity.

The above objects of the present invention are accomplished by a light-sensitive material comprising a support having thereon at least one light-sensitive silver halide emulsion layer, wherein said light-sensitive material contains a DIR coupler represented by formula (I):

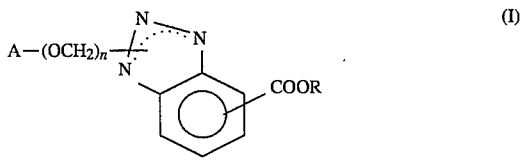

(I)

wherein A represents a coupler residue; R represents an alkyl group having from 1 to 4 carbon atoms substituted with an alkoxycarbonyl group or an alkyl carbamoyl group; and n represents 1 when A represents a phenol type or naphthol type coupler residue, or n represents 0 when A represents other coupler residues, and said emulsion layer contains chemically sensitized silver halide grains which individually have a distinct stratiform structure comprising silver iodobromide containing from 7 to 45 mol % of silver iodide and which individually have an overall silver iodide content of more than 4 mol %.

DETAILED DESCRIPTION OF THE INVENTION

In formula (I), the coupler residue as represented by A includes a yellow coupler residue (e.g., open-chain ketomethylene type), a magenta coupler residue (e.g., 5-pyrazolone type, pyrazoloimidazole type, pyrazolotriazole type), a cyan coupler residue (e.g., phenol type, naphthol type), and a colorless coupler residue (e.g., indanone type, acetophenone type). Also included in the coupler residue A are hetero ring type coupler residues as described in U.S. Pat. Nos. 4,315,070, 4,183,752, 3,961,959, and 4,171,223.

Of these coupler residues preferred are those having formulae (Cp-1), (Cp-2), (Cp-3), (Cp-4), (Cp-5), (Cp-6), (Cp-7), (Cp-8), (Cp-9) or (Cp-10) shown below because of their high coupling rate.

(Cp-1)

-continued (Cp-2)
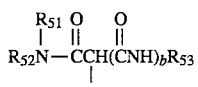

(Cp-3)
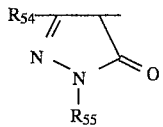

(Cp-4)
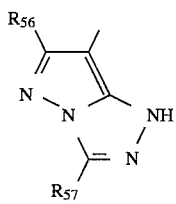

(Cp-5)
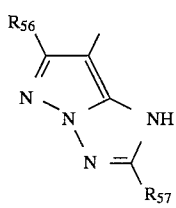

(Cp-6)
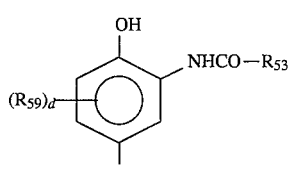

(Cp-7)
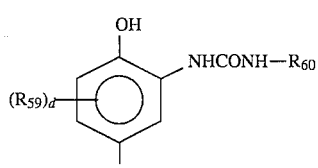

(Cp-8)
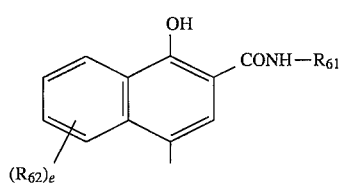

(Cp-9)
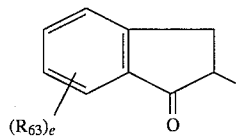

(Cp-10)
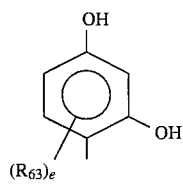

In formulae (Cp-1) through (Cp-10), each free bond indicates a coupling position at which a coupling releasable group is bonded. Where $R_{51}$, $R_{52}$, $R_{53}$, $R_{54}$, $R_{55}$, $R_{56}$, $R_{57}$, $R_{58}$, $R_{59}$, $R_{60}$, $R_{61}$, $R_{62}$, or $R_{63}$ contains an antidiffusion group, it is selected so as to have a total carbon atom number of from 8 to 40, and preferably from 10 to 30. Otherwise, it preferably has a total carbon atom number of not more than 15. In the case of couplers of bis form, telomer form, or polymer form, any of these groups represents a divalent group for linking a repeating unit. In this case, the total carbon atom number in each of $R_{51}$ to $R_{63}$ may be out of the above-mentioned range.

In what follows, definitions for symbols $R_{51}$ to $R_{63}$, b, d, and e are described, wherein $R_{41}$ represents an aliphatic group, an aromatic group, or a heterocyclic group; $R_{42}$ represents an aromatic group or a heterocyclic group; and $R_{43}$, $R_{44}$, and $R_{45}$ each represent a hydrogen atom, an aliphatic group, an aromatic group, or a heterocyclic group.

$R_{51}$ has the same meaning as $R_{41}$. b represents 0 or 1. $R_{52}$ and $R_{53}$ each have the same meaning as $R_{42}$. $R_{54}$ has the same meaning as $R_{41}$ or represents

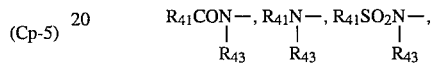

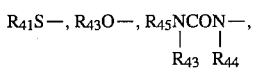

or N≡C—. $R_{55}$ has the same meaning as $R_{41}$. $R_{56}$ and $R_{57}$ each have the same meaning as $R_{43}$ or represent $R_{41}S$—, $R_{43}O$—,

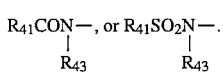

$R_{58}$ has the same meaning as $R_{41}$. $R_{59}$ has the same meaning as $R_{41}$ or represents

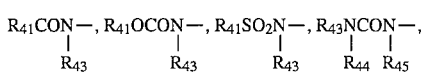

$R_{41}O$—, $R_{41}S$—, a halogen atom, or

d represents 0, 1, 2, or 3. When d is 2 or 3, plural $R_{59}$ may be the same or different, or each of them may represent a divalent group and be connected to each other to form a cyclic structure. Typical examples of such a divalent group for cyclization are:

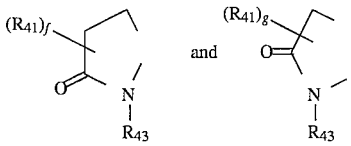

wherein f represents 0 or an integer of from 1 to 4; and g represents 0 or an integer of from 1 to 2. $R_{60}$ has the same meaning as $R_{41}$. $R_{61}$ has the same meaning as $R_{41}$. $R_{62}$ has the same meaning as $R_{41}$ or represents $R_{41}OCONH$—, $R_{41}SO_2NH$—, $$R_{43}NCON-, R_{43}NSO_2N-,$$
$$\quad |\quad |\qquad\quad |\quad |$$
$$\quad R_{44}\ R_{45}\qquad R_{44}\ R_{45}$$

$R_{43}O-$, $R_{41}S-$, a halogen atom, or $$R_{41}N-.$$
$$\ |$$
$$R_{43}$$

$R_{63}$ has the same meaning as $R_{41}$ or represents $$R_{43}CON-, R_{43}NCO-, R_{41}SO_2N-, R_{43}NSO_2-,$$
$$\quad |\quad |\qquad |\qquad\qquad |\qquad\qquad |$$
$$R_{44}R_{45}\quad R_{44}\qquad R_{44}\qquad R_{44}$$

$R_{41}SO_2-$, $R_{43}OCO-$, $R_{43}OSO_2-$, a halogen atom, a nitro group, a cyano group, or $R_{43}CO-$. e represents 0 or an integer of from 1 to 4. When e is 2 to 4, plural $R_{62}$ or $R_{63}$ may be the same or different.

The term "aliphatic group" as referred to above means a saturated or unsaturated, acyclic or cyclic, straight chain or branched, and substituted or unsubstituted aliphatic hydrocarbon group having from 1 to 32, preferably 1 to 22, carbon atoms. Typical examples of these aliphatic groups are methyl, ethyl, propyl, isopropyl, butyl, t-butyl, iso-butyl, t-amyl, hexyl, cyclohexyl, 2-ethylhexyl, octyl, 1,1,3,3-tetramethylbutyl, decyl, dodecyl, hexadecyl, and octadecyl groups.

The term "aromatic group" as referred to above means an aromatic group having from 6 to 20 carbon atoms, and preferably includes a substituted or unsubstituted phenyl or naphthyl group.

The term "heterocyclic group" as referred to above means a substituted or unsubstituted and, preferably, 3- to 8-membered heterocyclic group containing from 1 to 20, preferably from 1 to 7, carbon atoms and a hetero atom selected from a nitrogen atom, an oxygen atom, and a sulfur atom. Typical examples of such a heterocyclic group are 2-pyridyl, 2-thienyl, 2-furyl, 1,3,4-thiadiazol-2-yl, 2,4-dioxo-1,3-imidazolidin- 5-yl, 1,2,4-triazol-2-yl, and 1-pyrazolyl groups.

Substituents of the above-mentioned substituted aliphatic hydrocarbon groups, aromatic groups, or heterocyclic groups typically include a halogen atom, $R_{47}O-$, $R_{46}S-$, $$R_{47}CON-, R_{47}NCO-, R_{46}OCON-, R_{46}SO_2N-,$$
$$\quad |\qquad\quad |\qquad\qquad |\qquad\qquad |$$
$$R_{48}\qquad R_{48}\qquad R_{47}\qquad R_{47}$$

$$R_{47}NSO_2-, R_{46}SO_2-, R_{47}OCO-, R_{47}NCON-,$$
$$\quad |\qquad\qquad\qquad\qquad\qquad\qquad |\quad |$$
$$R_{48}\qquad\qquad\qquad\qquad\qquad\qquad R_{48}\ R_{49}$$

$$R_{46},\ \ \underset{R_{47}}{\diagup}\!\!\underset{\|O}{\overset{\overset{O}{\|}}{\diagdown}}\!\!N-,$$

$R_{46}COO-$, $R_{47}OSO_2-$, a cyano group, and a nitro group, wherein $R_{46}$ represents an aliphatic, aromatic or heterocyclic group; and $R_{47}$, $R_{48}$, and $R_{49}$ each represent an aliphatic, aromatic or heterocyclic group or a hydrogen atom. The meanings of the aliphatic group, aromatic group and heterocyclic group as used herein are the same as defined above.

$R_{51}$ preferably represents an aliphatic group or an aromatic group in formula (Cp-1) or a hydrogen atom or an aliphatic group in formula (Cp-2).

$R_{52}$, $R_{53}$, and $R_{55}$ each preferably represent a heterocyclic group or an aromatic group.

$R_{54}$ preferably represents $R_{41}CONH-$ or $$R_{41}-N-.$$
$$\quad\ \ |$$
$$\quad\ \ R_{43}$$

$R_{56}$ and $R_{57}$ each preferably represent an aliphatic group, an aromatic group, $R_{41}O-$, or $R_{41}S-$.

$R_{58}$ preferably represents an aliphatic group or an aromatic group.

In formula (Cp-6), $R_{59}$ preferably represents a chlorine atom, an aliphatic group, or $R_{41}CONH-$; and d preferably represents 1 or 2. In formula (Cp-7), $R_{59}$ preferably represents $R_{41}CONH-$; and d preferably represents 1.

$R_{60}$ preferably represents an aromatic group.

$R_{61}$ preferably represents an aliphatic group or an aromatic group.

In formula (Cp-8), e preferably represents 0 or 1; and $R_{62}$ preferably represents $R_{41}OCONH-$, $R_{41}CONH-$, or $R_{41}SO_2NH-$ and is preferably bonded at the 5-position of the naphthol ring.

In formula (Cp-9), $R_{63}$ preferably represents $R_{41}CONH-$, $R_{41}SO_2NH-$, $$R_{41}NSO_2-, R_{41}SO_2-, R_{41}NCO-,$$
$$\quad |\qquad\qquad\qquad\qquad\quad |$$
$$R_{43}\qquad\qquad\qquad\qquad R_{43}$$

a nitro group, or a cyano group.

In formula (Cp-10), $R_{63}$ preferably represents $$R_{43}NCO-,$$
$$\quad |$$
$$R_{43}$$

$R_{43}OCO-$, or $R_{43}CO-$.

The alkyl group as represented by R includes a straight chain or branched and substituted alkyl group having from 1 to 4 carbon atoms, and preferably from 1 to 3 carbon atoms. Substituents include an alkoxycarbonyl group having from 2 to 6 carbon atoms (e.g., methoxycarbonyl, propoxycarbonyl, butoxycarbonyl, isobutoxycarbonyl, isopropoxycarbonyl, pentyloxycarbonyl, isopentyloxycarbonyl, 2-methoxyethoxycarbonyl), or an alkyl carbamoyl group having up to 6 carbon atoms (e.g., N,N-diethylcarbamoyl, N-methyl-N-ethylcarbamoyl, pyrrolidinocarbonyl, piperidinocarbonyl).

Suitable substituents for a pyridyl group as represented by R include the groups above-enumerated as substituents for an alkyl group and, in addition, an aliphatic group having from 1 to 6 carbon atoms (e.g., methyl, ethyl).

Specific examples of R include —$CH_2COOC_3H_7$, —$CH_2COOC_4H_9$, —$CH_2COOC_3H_7(i)$, —$CH_2COOC_4H_9(i)$, —$CH_2COOC_5H_{11}$, —$CH_2COOC_5H_{11}(i)$, —$CH_2COOC_5H_{11}(t)$, —$CH_2CH_2COOC_3H_7$, —$CH_2CH_2COOC_3H_7(t)$, —$CH_2CH_2CH_2COOCH_3$,

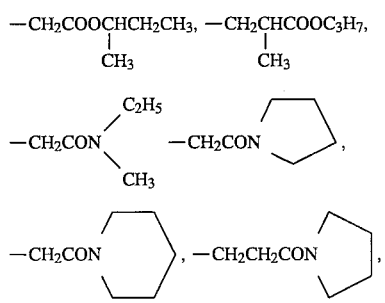
—CH₂CONHC₄H₉,   —CH₂CONHC₅H₁₁,
—CH₂CONHC₄H₉(i),
Specific examples of the DIR coupler represented by formula (I) are shown below for illustration.
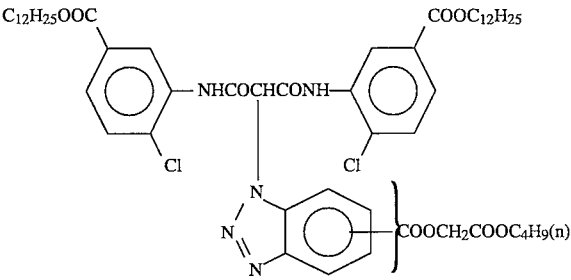
(D-1)
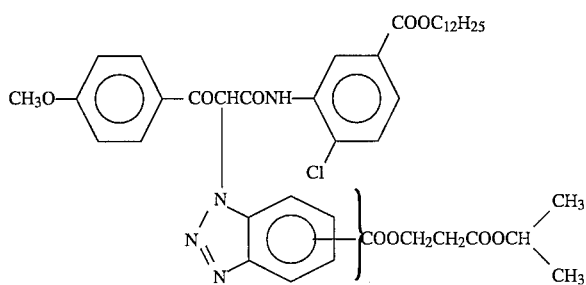
(D-2)
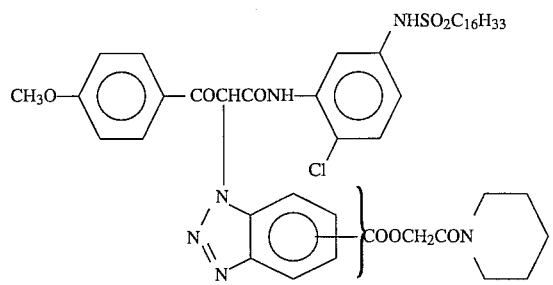
(D-3)
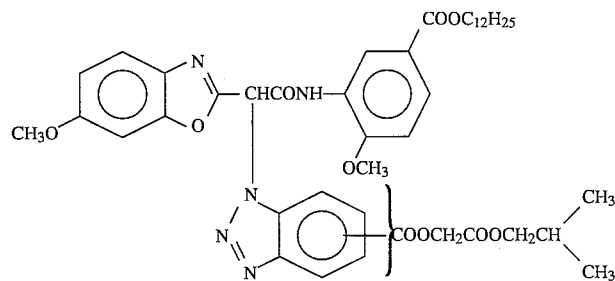
(D-4)

-continued
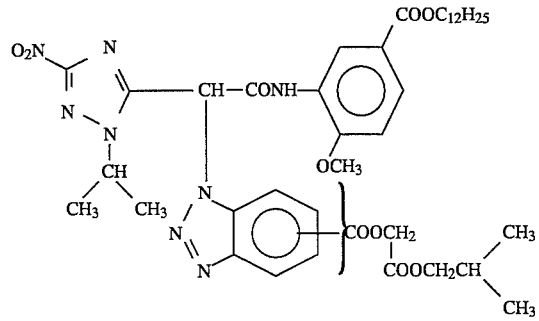 (D-5)
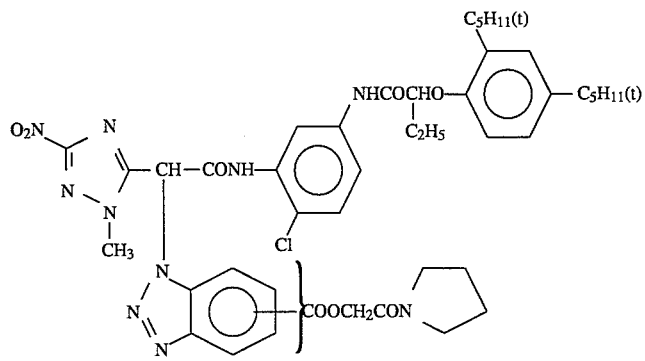 (D-6)
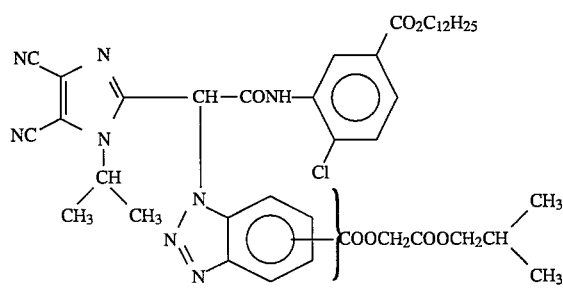 (D-7)
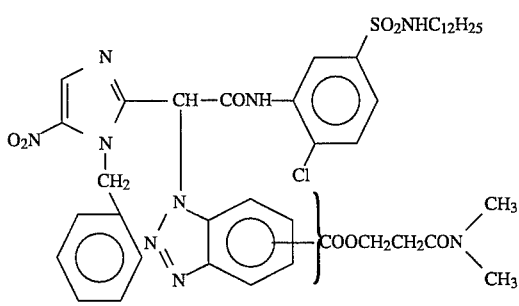 (D-8)
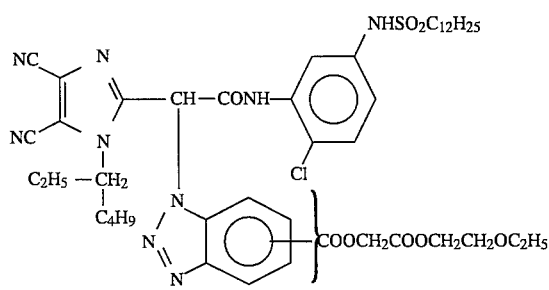 (D-9)

-continued
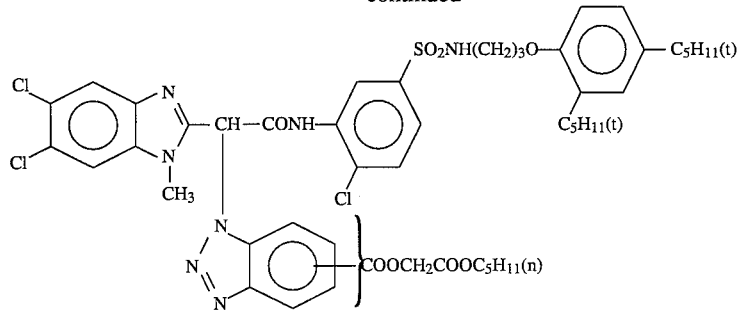 (D-10)
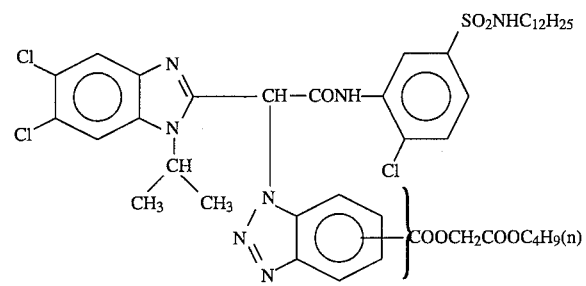 (D-11)
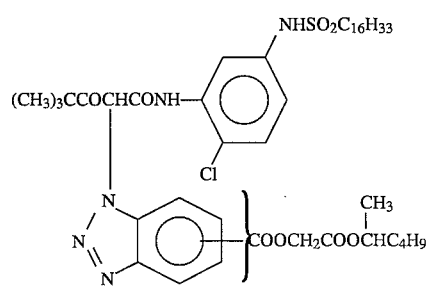 (D-12)
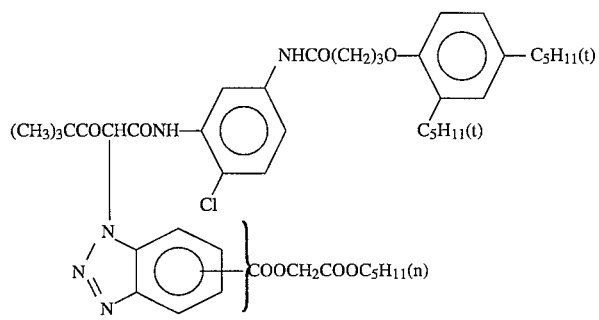 (D-13)
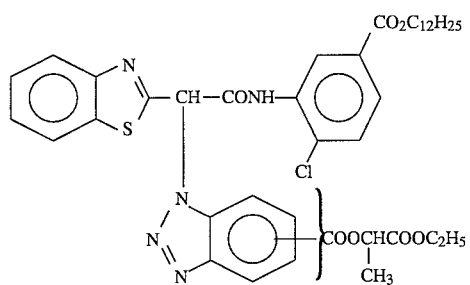 (D-14)
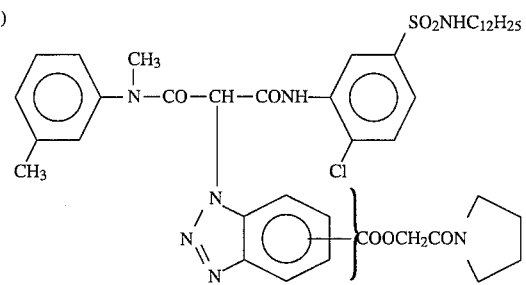 (D-15)

-continued
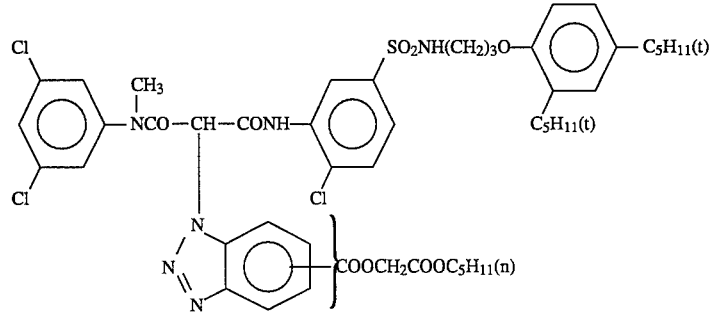
(D-16)
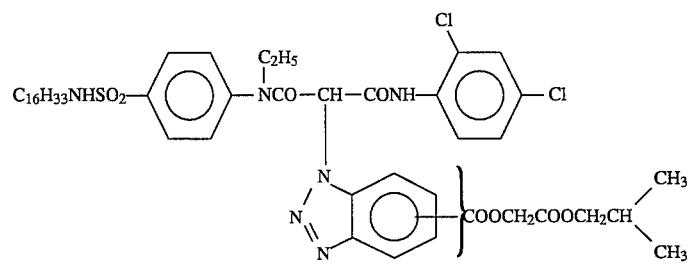
(D-17)
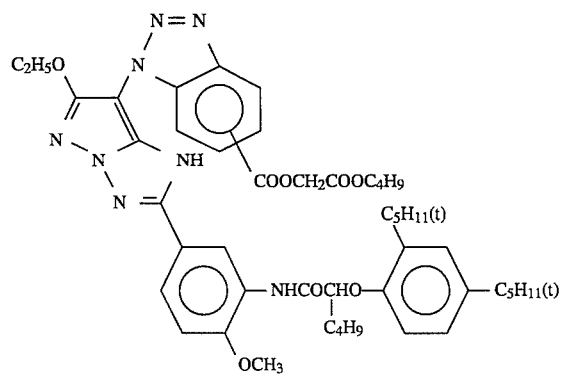
(D-18)
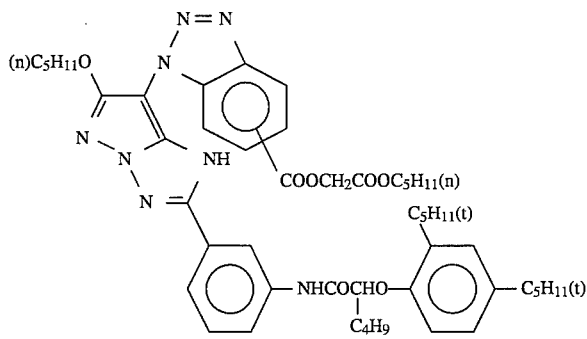
(D-19)
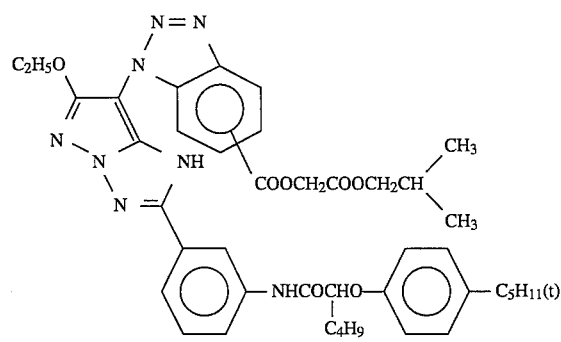
(D-20)

-continued
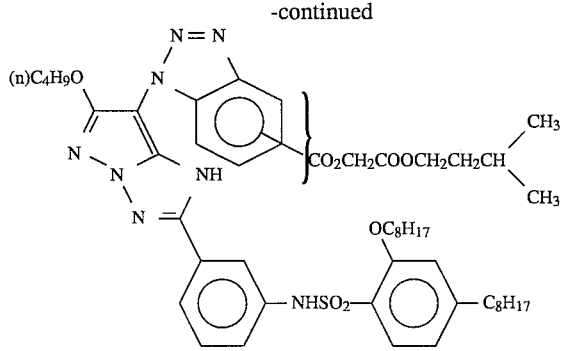
(D-21)
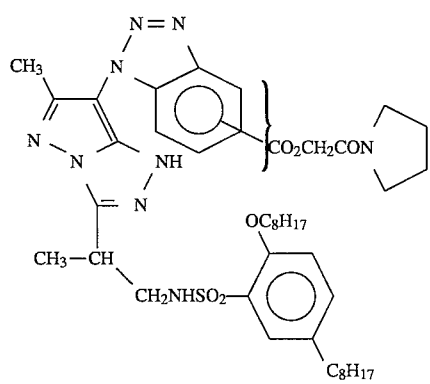
(D-22)
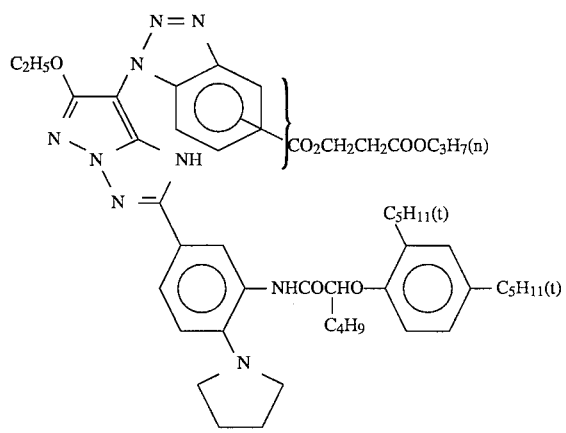
(D-23)
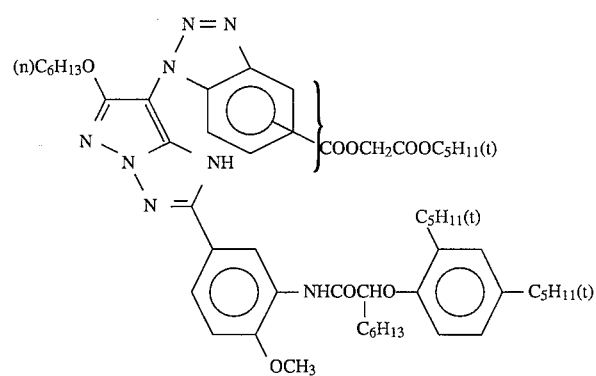
(D-24)

-continued
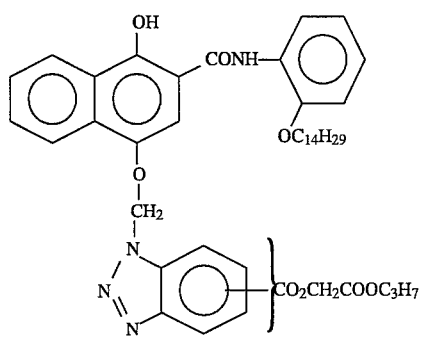 (D-25)
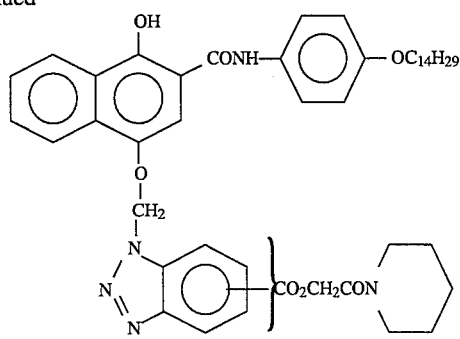 (D-26)
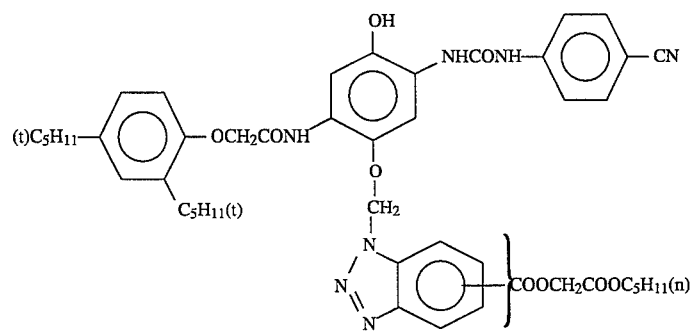 (D-27)
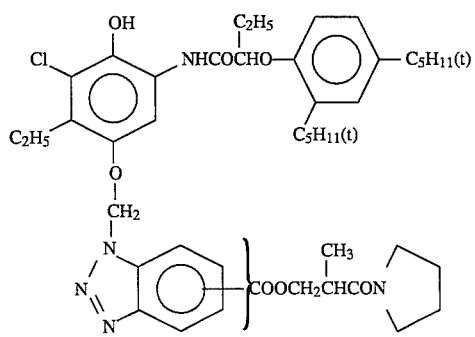 (D-28)
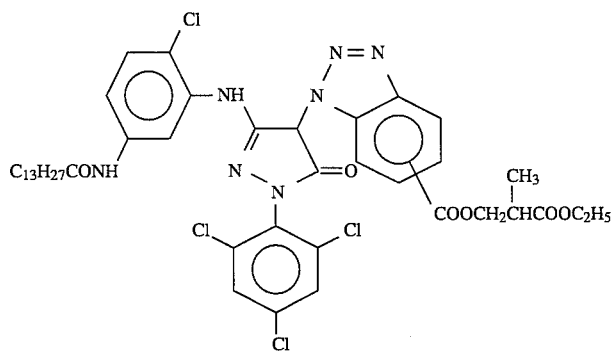 (D-29)
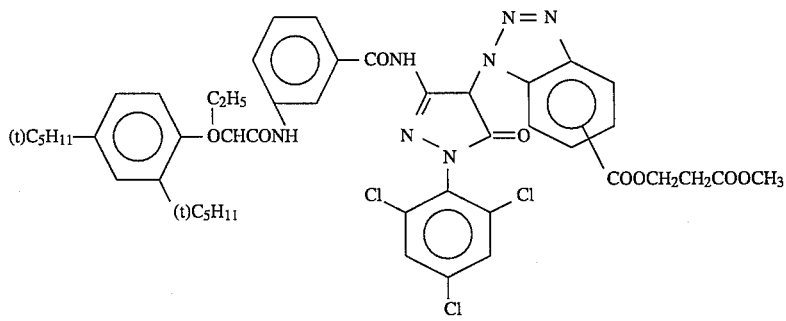 (D-30)

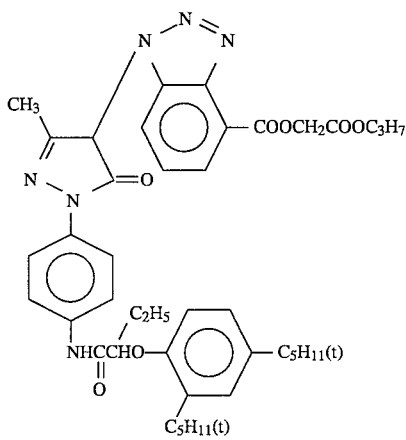

(D-31)

The compound represented by formula (I) can be synthesized by known processes disclosed, e.g., in JP-A-57-151944, EP 336411A, and EP 320939A. Synthesis examples of some of the compounds of formula (I) are described below for illustration.

SYNTHESIS EXAMPLE 1

Synthesis of Compound (D-1)

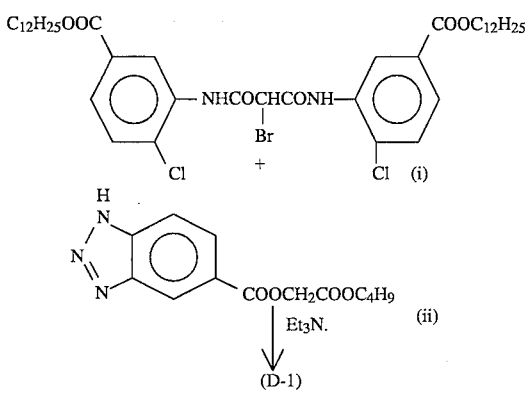

To 200 ml of N,N-dimethylformamide were added 13.5 g of compound (ii) and 4.9 g of triethylamine, and the mixture was stirred at room temperature for 15 minutes. To the resulting solution was added 20 g of compound (i), followed by stirring at room temperature for 3 hours. To the reaction mixture was added 500 ml of ethyl acetate, and the mixture was transferred to a separatory funnel and washed with water. The oily phase was separated and washed successively with diluted hydrochloric acid and water. The oily phase was then distilled under reduced pressure to remove the solvent. To the residue was added 100 ml of a mixed solvent of ethyl acetate and hexane, and precipitated crystals were collected by filtration to obtain 15.3 g of compound (D-1).

SYNTHESIS EXAMPLE 2

Synthesis of Compound (D-6)

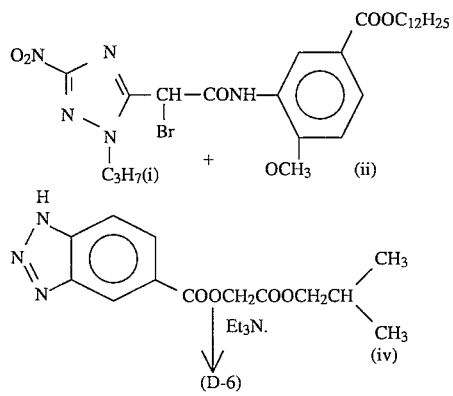

The reaction was carried out in the same manner as in Synthesis Example 1, except for replacing compound (ii) with an equivalent amount of compound (iv) and using 14.8 g of compound (iii) in place of compound (i). The reaction mixture was crystallized from a mixed solvent of isopropanol and hexane to obtain 8.5 g of compound ( D-6 ).

SYNTHESIS EXAMPLE 3

Synthesis of Compound (D-8)

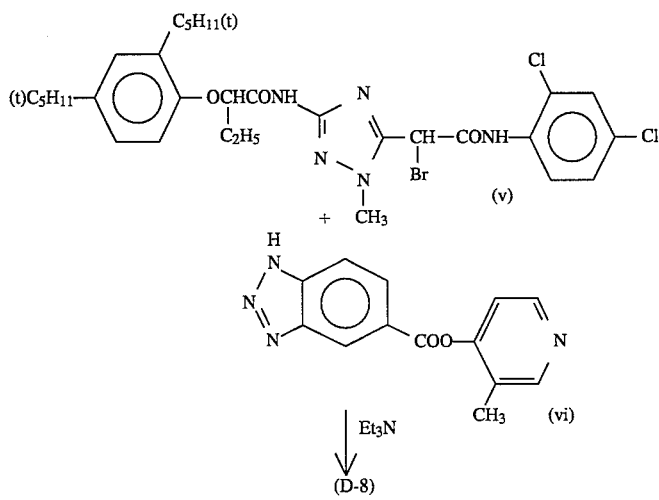

The reaction was carried out in the same manner as in Synthesis Example 1, except for using 16.5 g of compound (v) in place of compound (i) and using 12.3 g of compound (vi) in place of compound (ii). The reaction product was crystallized from a mixed solvent of ethyl acetate and hexane to obtain 9.8 g of compound (D-8).

SYNTHESIS EXAMPLE 4

Synthesis of Compound (D-9)

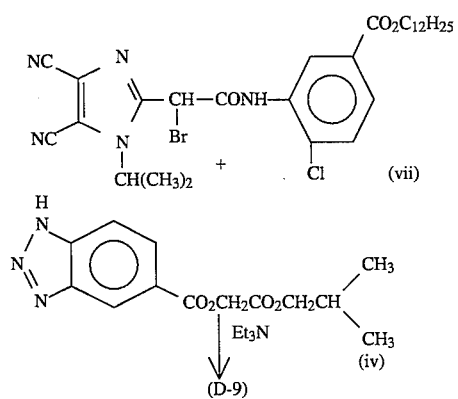

The reaction was carried out in the same manner as in Synthesis Example 1, except for using 15.0 g of compound (vii) in place of compound (iii), to obtain 12.1 g of compound (D-9).

SYNTHESIS EXAMPLE 5

Synthesis of Compound (D-17)

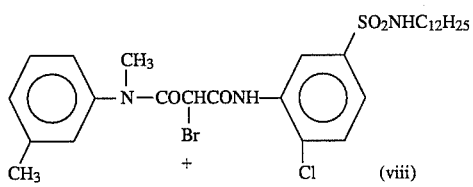

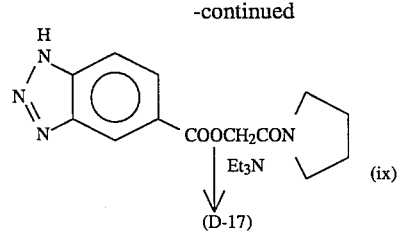

To 200 ml of N,N-dimethylacetamide were added 17.1 g of compound (ix) and 6.3 g of triethylamine, followed by stirring for 15 minutes. To the resulting solution was added dropwise a solution of 20 g of compound (viii) in 100 ml of chloroform over 20 minutes at room temperature. The reaction mixture was allowed to react at room temperature for 3 hours and then at 40° C. for 30 minutes. After the reaction, the reaction mixture was worked up in the same manner as in Example 1. Crystallization from a mixed solvent of ethyl acetate and hexane gave 15.3 g of compound (D-17).

SYNTHESIS EXAMPLE 6

Synthesis of Compound (D-23)

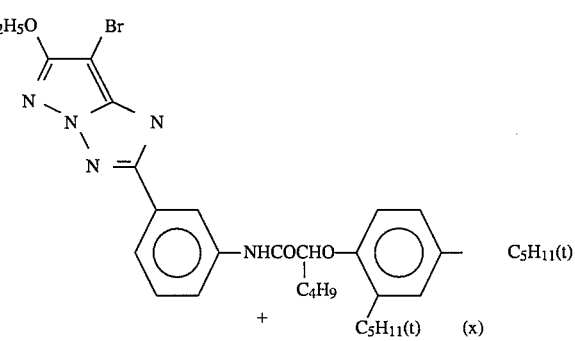

-continued

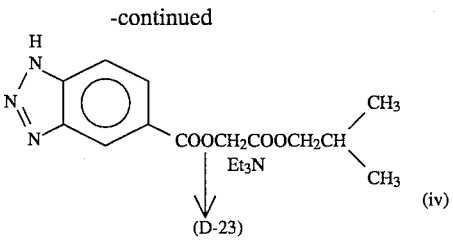

In 100 ml of N,N'-dimethyl-2-imidazolidinone was dissolved 25.5 g of compound (iv), and the solution was ice-cooled. To the solution was added 3.7 g of sodium hydride (60%), followed by stirring for 20 minutes. To the solution was added 20 g of compound (x), and the mixture was allowed to react at room temperature for 5 hours and then heated to 50° C., at which it was stirred for 1.5 hours. After the reaction, the reaction mixture was allowed to cool to room temperature, and 200 ml of ethyl acetate and 200 ml of water were added thereto. The reaction mixture was put in a separatory funnel. The oily phase was washed successively with water, diluted hydrochloric acid, and water. The oily phase was separated and distilled under reduced pressure to remove the solvent. The residue was crystallized from ethyl acetate and hexane, and the crystals were collected by filtration to obtain 15.5 g of compound (D- 23).

The coupler of formula (I) according to the present invention can be incorporated into any of the layers which constitute a light-sensitive material but is preferably added to a light-sensitive silver halide emulsion layer and/or an adjacent layer thereof, and more preferably to a light-sensitive silver halide emulsion layer. Where a light-sensitive silver halide emulsion layer containing the specific silver halide grains according to the present invention is comprised of two or more layers of different sensitivity, the coupler of formula (I) is most preferably added to a layer or layers other than the layer having the highest sensitivity.

The total amount of the coupler of formula (I) to be used in a light-sensitive material is usually from $3\times10^{-7}$ to $1\times10^{-3}$ mol/m$^2$, preferably from $3\times10^{-6}$ to $5\times10^{-4}$ mol/m$^2$, and more preferably from $1\times10^{-5}$ to $2\times10^{-4}$ mol/m$^2$.

The coupler of formula (I) can be incorporated into a light-sensitive material in a usual manner as hereinafter described.

It is essential that the emulsion layer according to the present invention should contain chemically sensitized silver halide grains which individually have a distinct stratiform structure comprising silver iodobromide containing from 7 to 45 mol % of silver iodide and which individually have an overall silver iodide content of more than 4 mol %.

The existence of a "distinct stratiform structure" as referred to herein can be appreciated by X-ray diffractiometry. Application of X-ray diffractiometry to analysis of silver halide grains is described, e.g., in H. Hirsch, *Journal of Photographic Science,* Vol. 10, p. 129 ff. (1962). On deciding the lattice constant depending on a halogen composition, diffraction peaks appear at an angle of diffraction satisfying Bragg's formula ($2d\sin\theta=n\lambda$).

For details of X-ray diffractiometry, reference can be made, e.g., to *Kisobunseki Kagaku Koza* 24, "X-sen Kaisetsu", Kyoritsu Shuppan and *X-sen Kaisetsu no Tebiki,* Rigaku Denki K.K. In a standard method, a diffraction pattern Of the (220) face of silver halide grains is obtained by using Cu as an anticathode and K$_\beta$-rays as a ray source (tube voltage: 40 kV; tube current: 60 mA). In order to increase the resolving power of a diffractiometer, a width of a slit (emission slit, receptor slit, etc.), a time constant of the apparatus, a scanning speed of a goniometer, and a recording speed should be properly selected, and a measurement precision should be confirmed by using a standard sample, e.g., silicon.

The terminology "distinct stratiform structure" as used herein means that analysis under x-ray diffractiometry shows a diffraction intensity vs. diffraction angle curve of a (220) face of silver halide (obtained by using K$_\beta$ rays of Cu at a diffraction angle ($2\theta$) between 38° and 42° C.) with at least two peaks, one corresponding to a high iodide layer having a silver iodide content of from 7.0 to 45 mol %, and the other corresponding to a low iodide layer having a silver iodide content of less than 7 mol %, and one minimum between the two peaks, the diffraction intensity of the peak corresponding to the high iodide layer being from 1/10 to 3/1, preferably from 1/5 to 3/1, and more preferably from 1/3 to 3/1, that corresponding to the low iodide layer.

It is preferable that the minimum diffraction intensity between two peaks is within 90%, more preferably within 80%, and most preferably within 60%, of that of the lower one of the two or more peaks.

A technique for resolving a diffraction curve comprised of two diffraction components is well known and described, e.g., in *Jikken Butsurigaku Koza* 11, "Koshi Kekkan", Kyoritsu Shuppan.

It is also useful to analyze the curve with a curve analyzer produced by E.I. du Pont, assuming the curve as a Gauss function or a Lorenz function.

An emulsion containing two kinds of silver halide grains both of which have no distinct stratiform structure and which differ from each other in halogen composition does not produce any excellent effects on photographic performance as obtained in the present invention. However, an X-ray diffraction curve of such an emulsion also reveals two peaks. Whether a silver halide emulsion is an emulsion according to the present invention or an emulsion containing two different kinds of silver halide grains as described above can be judged by combining the above-described X-ray diffractometry with a method using an electron-probe microanalyzer (hereinafter abbreviated as an EPMA method).

To carry out an EPMA method, an emulsion sample in which silver halide grains are well dispersed so as not to contact with each other is prepared, and an electron beam is irradiated thereon. Elemental analysis of an extremely fine part can be made by X-ray analysis with the excited electron beam. Thus, a halogen composition of individual grains can be decided by obtaining intensities of characteristic X-rays of silver and iodine emitted from each lattice. EPMA analysis on at least 50 grains would suffice for judging whether or not a sample emulsion is the emulsion according to the present invention.

The emulsion of the present invention preferably has a uniform iodide content among grains. More specifically, the iodide content distribution among grains as determined by the EPMA method preferably has a relative standard deviation of not more than 50%, and more preferably not more than 35%.

Another preferred iodide distribution among grains is such that logarithms of grain size have a positive correlation with iodide contents. Namely, larger size grains have higher iodide contents, and smaller size grains have lower iodide contents. An emulsion having such a correlation gives favorable results of graininess. The coefficient of correlation is preferably 40% or more, and more preferably 50% or more.

In individual grains, the core comprises, in addition to silver iodobromide, either silver chlorobromide and/or silver bromide, with a proportion of silver bromide being preferably higher. The silver iodide content in the core ranges from 7.0 to 45 mol %, preferably from 15 to 45 mol %, and more preferably from 25 to 45 mol %. The most preferred halogen composition of the core is silver iodobromide having a silver iodide content of from 30 to 45 mol %.

The outermost layer of individual grains comprises silver halide having a silver iodide content of not more than 7.0 mol %, and preferably not more than 5.0 mol %.

Silver halide other than silver iodide in the outermost layer may be any of silver chloride, silver chlorobromide, and silver bromide, with a proportion of silver bromide preferably being higher. The most preferred halogen composition of the outermost layer is silver bromide or silver iodobromide containing from 0.5 to 5.0 mol % of silver iodide.

The overall halogen composition in individual grains should have a silver iodide content exceeding 4.0 mol %, preferably of from 6.0 to 25 mol %, more preferably from 8.0 to 20 mol %, and most preferably from 10 to 25 mol %.

While the graininess of the silver halide emulsion used in the present invention is improved partly because a high iodide content can be realized without reducing developing activity to thereby increase light absorption, it is believed that the improvement owes much more to the distinct stratiform structure comprising a high iodide layer as a core and a low iodide layer as an outermost layer which leads to an increase in efficiency of latent image formation.

The silver halide grains having a distinct stratiform structure have a mean grain size of from 0.05 to 3.0 μm, preferably from 0.1 to 1.5 μm, more preferably from 0.2 to 1.3 μm, and most preferably from 0.3 to 1.2μm.

The terminology "mean grain size" as used herein means a geometrical mean of grain size well-known in the art as described in T. H. James, et al., *The Theory of the Photographic Process,* The 3rd Ed., p. 39, MacMillan (1966). The terminology "grain size" as used herein means a sphere-equivalent diameter as described in Arakawa Masafumi, *Ryudo Sokutei Nyumon,* Vol. 17, pp. 299–313, Funtai Kogakukai (1980). The grain size can be measured by, for example, a Coulter counter method, a single particle ray scattering method, a laser ray scattering method, etc.

The silver halide grains having a distinct stratiform structure may have a regular crystal form, such as a hexahedral form, an octahedral form, a dodecahedral form, and a tetradecahedral form, or an irregular crystal form, such as a spherical form, a potato-like form, and a tabular form. Tabular twins having an aspect ratio of from 1.2 to 8, and particularly from 1.5 to 5 are especially preferred.

The crystal grains, either of regular or irregular form, preferably have 50% or more of a (111) face are particularly preferred. The facial ratio of a (111) face can be determined by a dyestuff adsorption method of Kubelka-Munk. In carrying out the dyestuff adsorption method, a dyestuff which is adsorbed preferentially onto either a (111) face or a (100) face to exhibit a spectral difference in association state between on the (111) face and on the (100) face is selected. Such a dyestuff is added to an emulsion, and the spectral characteristics plotted against the amount of the dyestuff added are closely examined to decide a facial ratio of the (111) face.

The emulsion according to the present invention may be used in any silver halide light-sensitive layer of a light-sensitive material, but is preferably used in a blue- or green-sensitive emulsion layer. Where a blue- or green-sensitive emulsion layer is composed of two or more layers different in sensitivity, the emulsion of the invention is preferably used in a layer other than the layer having the lowest sensitivity.

In the present invention, it is particularly preferable to use a compound represented by formula (A) shown below for ensuring high sensitivity, improving graininess and preservability of a light-sensitive material, and reducing variations in photographic performance of a processing solution.

wherein Q represents a heterocyclic ring residue having directly or indirectly bonded thereto at least one group selected from the group consisting of $-SO_3M^2$, $-COOM^2$, $-OH$, and $-NR^1R^2$; $M^1$ and $M^2$ each represent a hydrogen atom, an alkali metal, a quaternary ammonium group, or a quaternary phosphonium group; and $R^1$ and $R^2$ each represent a hydrogen atom or a substituted or unsubstituted alkyl group, having from 1 to 4 carbon atoms.

The compound represented by formula (A) is considered to be endowed with water solubility or improved water solubility under the pH condition in a developing solution and thereby run out into a developing solution in other words, if the compound of formula (A) is incorporated into a light-sensitive material, it is expected to be dissolved in a developing solution to contaminate the developing solution. It is surprising that a variation in characteristics of development finish is nevertheless small with reduced fog. Such unexpected results appear to arise from a large difference in behavior of the compound (A) between when it is present within a light-sensitive material and when it runs out into a developing solution. Anyway, the mechanism of the effects of the compound (A) is still unclear and would be elucidated through future study.

In formula (A), examples of the heterocyclic residue as represented by Q include oxazole, thiazole, imidazole, selenazole, triazole, tetrazole, thiadiazole, oxadiazole, pentazole, pyrimidine, thiazoa, triazine, and thiadiazine rings, each of which may be condensed with other carbon rings or hetero rings to form a benzothiazole, benzotriazole, benzimidazole, benzoxazole, benzoselenazole, naphthoxazole, triazaindolidine, diazaindolidine, or tetraazaindolidine ring.

Of the mercapto heterocyclic compounds represented by formula (A) particularly preferred are those represented by formulae (B) and (C):

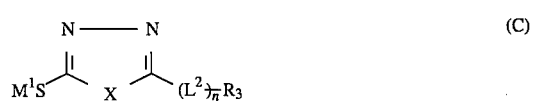

In formula (B), Y and Z each represent a nitrogen atom or $CR^4$, wherein $R^4$ represents a hydrogen atom, a substituted or unsubstituted alkyl group, or a substituted or unsubstituted aryl group; $R^3$ represents an organic residue, specifically an alkyl group having from 1 to 20 carbon atoms (e.g., methyl, ethyl, propyl, hexyl, dodecyl, octadecyl) or an aryl group having from 6 to 20 carbon atoms (e.g., phenyl, naphthyl), which is substituted with at least one group selected from the group consisting of —SO$_3$M$^2$, —COOM$^2$, —OH, and —NR$^1$R$^2$; —L$^1$— represents a linking group selected from the group consisting of —S—, —O—,

—CO—, —SO—, and —SO$^2$—; n represents 0 or 1; and M$^1$, M$^2$, R$^1$, and R$^2$ are as defined above.

The alkyl or aryl group in R$^3$ may further have other substituents, such as a halogen atom (e.g., F, Cl, Br), an alkoxy group (e.g., methoxy, methoxyethoxy), an aryloxy group (e.g., phenoxy), an alkyl group (for an aryl group of R$^3$), an aryl group (for an alkyl group of R$^3$), an amido group (e.g. acetamido, benzoylamino), a carbamoyl group (e.g., unsubstituted carbamoyl, phenylcarbamoyl, methylcarbamoyl), a sulfonamido group (e.g., methanesulfonamido, phenylsulfonamido), a sulfamoyl group (e.g., unsubstituted sulfamoyl, methylsulfamoyl, phenylsulfamoyl), a sulfonyl group (e.g., methylsulfonyl, phenylsulfonyl), a sulfinyl group (e.g., methylsulfinyl, phenylsulfinyl), a cyano group, an alkoxycarbonyl group (e.g., methoxycarbonyl), an aryloxycarbonyl group (e.g., phenoxycarbonyl), a nitro group, etc.

Where R$^3$ has two or more substituents selected from —SO$_3$M$^2$, —COOM$^2$, —OH, and —NR$^1$R$^2$, these substituents may be the same or different.

In formula (C), X represents a sulfur atom, an oxygen atom, or

R$^5$ represents a hydrogen atom, a substituted or unsubstituted alkyl group, or a substituted or unsubstituted aryl group; L$^2$ represents —CONR$^6$—, —NR$^6$CO—, —SO$_2$NR$^6$—, —NR$^6$SO$_2$—, —OCO—, —S—, —NR$^6$—, —CO—, —SO—, —OCOO—, —NR$^6$CONR$^7$—, —NR$^6$COO—, —OCONR$^6$—, or —NR$^6$SO$_2$NR$^7$—; R$^6$ and R$^7$ each represent a hydrogen atom, a substituted or unsubstituted alkyl group, or a substituted or unsubstituted aryl group; and R$^3$, M$^1$, M$^2$, are as defined above and n represents 0 or 1.

The alkyl group or aryl group as represented by R$^4$, R$^5$, R$^6$, or R$^7$ may have substituents selected from those enumerated above with respect to R$^3$.

Of the compounds of formulae (B) and (C), those wherein R$^3$ is an organic residue substituted with —SO$_3$M$^2$ or —COOM$^2$.

Preferred examples of the compounds represented by formula (A) are shown below for illustration.

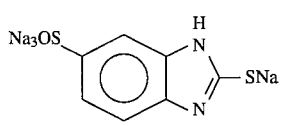

(1)

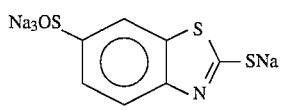

(2)

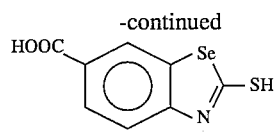

(3)

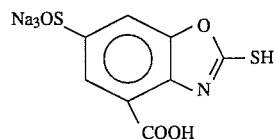

(4)

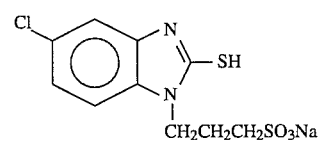

(5)

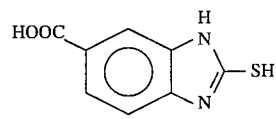

(6)

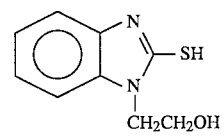

(7)

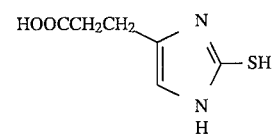

(8)

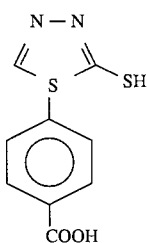

(9)

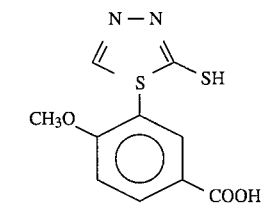

(10)

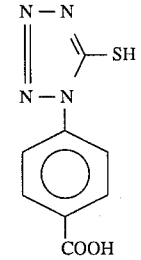

(11)

-continued

(12) 3-(5-mercapto-1-tetrazolyl)benzoic acid structure

(13) 4-chloro-3-(5-mercapto-1-tetrazolyl)benzoic acid structure

(14) 3,5-dicarboxy-1-(5-mercaptotetrazolyl)benzene structure

(15) 3-(5-mercapto-1-tetrazolyl)-4-hydroxybenzoic acid structure

(16) 3,5-dihydroxy-1-(5-mercapto-1-tetrazolyl)benzene structure

(17) sodium 4-(5-thio-1-tetrazolyl)benzenesulfonate structure

(18) sodium 3-(5-thio-1-tetrazolyl)benzenesulfonate structure

(23) sodium 3-(5-mercapto-1,3,4-thiadiazol-2-yl)benzenesulfonate structure

(24) 1-(2-dimethylaminoethyl)-5-mercaptotetrazole structure

(25) 1-(2-carboxyethyl)-5-phenyl-3-mercapto-1,2,4-triazole structure

(26) 1-(3,5-dicarboxyphenyl)-2-mercaptoimidazole structure

(27) sodium 3-(2-thio-1-imidazolyl)benzenesulfonate structure

(28) 2-mercapto-5-(carboxymethylthio)-1,3,4-thiadiazole structure

(29) 2-mercapto-5-(1,2-dicarboxyethylthio)-1,3,4-thiadiazole structure

(30) sodium 2-mercapto-5-(4-sulfobutylthio)-1,3,4-thiadiazole structure

(31) sodium 2-mercapto-5-(2-sulfoethylthio)-1,3,4-thiadiazole structure

(32) 2-mercapto-5-(3-carboxypropanoylamino)-1,3,4-thiadiazole structure

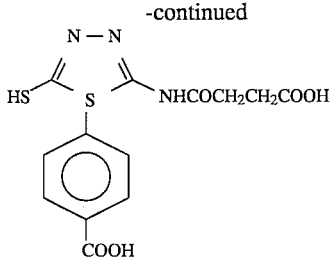 (38)

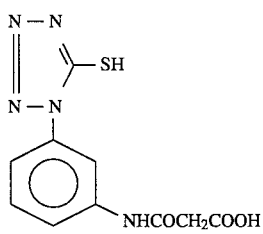 (39)

The compounds of formula (I) are known compounds and can be synthesized by known processes. Literatures referring to the synthesis of the compounds of formula (I) are listed below.

U.S. Pat. Nos. 2,585,388 and 2,541,924, JP-B-42- 21842 (the term "JP-B" as used herein means an "examined published Japanese patent application"), JP-A-53-50169, British Patent 1,275,701, D. A. Berges, et al., *Journal of the Heterocyclic Chemistry*, No. 15, p. 981 (1978), *The Chemistry of Heterocyclic Chemistry*, "Imidazole and Derivatives Part I", pp. 336–339, *Chemical Abstract*, Vol. 58, No. 7921, p. 394 (1963), E. Hoggarth, *Journal of Chemical Society*, pp. 1160–1167 (1949), S. R. Saudler & W. Karo, *Organic Functional Group Preparation*, pp. 312–315, Academic Press (1968), M. Chamdon, et al., *Bulletin de la Societe Chimique de France*, p. 723 (1954), D. A. Shirley & D. W. Alley, *J. Amer. Chem. Soc.*, Vol. 79, p. 4922 (1954), A. Wohl & W. Marchwald, *Ber.* (Jounal of Chemical Society, German), Vol. 22, p. 568 (1889), *J. Amer. Chem. Soc.*, Vol. 44, p. 1502–1510, U.S. Pat. No. 3,017,270, British Patent 940, 169, JP-B-49-8334, JP-A-55-59463, *Advanced in Heterocyclic Chemistry*, Vol. 9, pp. 165–209 (1968), West German Patent 2,716,707, *The Chemistry of Heterocyclic Compounds Imidazole and Derivatives*, Vol. 1, p. 384, *Org. Synth.*, Vol. IV, p. 569 (1963), *Ber.*, Vol. 9, p. 465 (1976), *J. Amer. Chem. Soc.*, Vol. 45, p. 239 (1923), JP-A-50-89034, JP-A-53- 28426, JP-A-55-21007, JP-B-40-28496.

The compound of formula (A) is incorporated into silver halide emulsion layers or hydrophilic colloidal layers (e.g., intermediate layers, surface protective layers, yellow filter layers, antihalation layers), and preferably a silver halide emulsion layer or an adjacent layer thereof.

The compound of formula (A) is used in an amount of from $1\times10^{-7}$ to $1\times10^{-3}$ mol/m$^2$, preferably from $5\times 10^{-7}$ to $1\times10^{-4}$ mol/m$^2$, and more preferably from $1\times 10^{-6}$ to $3\times10^{-5}$ mol/m$^2$.

The emulsion containing the specific silver halide grains according to the present invention is preferably a mono-dispersed emulsion. The terminology "mono-dispersed emulsion" as used herein means an emulsion whose grain size distribution has a coefficient of variation (S/r̄) of not more than 0.25, wherein r̄ is a mean grain size, and S is a standard deviation for grain size. That is, a grain size of individual grains being taken as ri, and the number of grains being taken as ni, a mean grain size r is defined by equation:

$$\bar{r}=\frac{\Sigma ni \times ri}{\Sigma ni}$$

Accordingly, the standard deviation S is defined by equation:

$$S=\sqrt{\frac{\Sigma (\bar{r}-ri)^2 \times ni}{\Sigma ni}}$$

The terminology "grain size of individual grains" as used herein means a projected area-equivalent diameter of a microphotograph taken by a well-known technique (usually electron microphotography) as described in T. H. James, et. al., *The Theory of the Photographic Process*, The 3rd Ed., pp. 36–43, MacMillan (1966). The terminology "projected area-equivalent diameter" as used herein is defined as a diameter of a circle having the same area as the projected area of a silver halide grain as described in the reference supra. Therefore, even if silver halide grains have a form other than a spherical form (e.g., a cubic form, an octahedral form, a tetradecahedral form, a tabular form, a potato-like form), a mean grain size r̄ and its standard deviation S can be obtained as described above.

The silver halide grains have a coefficient of variation of grain size of not more than 0.25, preferably not more than 0.20, and more preferably not more than 0.15.

In the present invention, it is more preferable for further improving sharpness to incorporate a polymer coupler comprising a monomer represented by formula (PA) shown below into a green-sensitive layer. If a light-sensitive material containing a conventional hydrolyzable DIR coupler is processed while replenishing a developing solution, there is observed an increase in contrast which seems attributed to the above-described polymer coupler. On the contrary, the light-sensitive material containing the DIR coupler represented by formula (I) according to the present invention does not suffer from such a phenomenon. That is, use of the DIR coupler of formula (I) makes it possible to freely use such a polymer coupler.

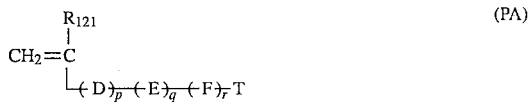 (PA)

wherein $R_{121}$ represents a hydrogen atom, an alkyl group having from 1 to 4 carbon atoms, or a chlorine atom; —D— represents —COO—, —CONR$_{122}$—, or a substituted or unsubstituted phenyl group; —E— represents a substituted or unsubstituted alkylene group, a substituted or unsubstituted phenylene group, or a substituted or unsubstituted aralkylene group; —F— represents —CONR$_{122}$—, —NR$_{122}$CONR$_{122}$—, —NR$_{122}$COO—, —NR$_{122}$CO—, —OCONR$_{122}$—, —NR$_{122}$—, —COO—, —OCO—, —CO—, —O—, —S—, —SO$_2$—, —NR$_{122}$SO$_2$—, or —SO$_2$NR$_{122}$—; $R_{122}$ represents a hydrogen atom, a substituted or unsubstituted aliphatic group, or a substituted or unsubstituted aryl group; plural $R_{122}$ groups, if any in the same molecule, may be the same or different; p, q, and r each represent 0 or 1, provided that they do not simultaneously represent 0; and T represents a magenta coupler residue represented by formula (PB) shown below which is bonded to the moiety at any of the Ar, Z, and $R_{133}$ moieties described below.

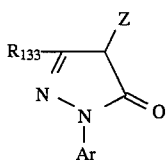
(PB)

wherein Ar represents a group known as a substituent at the 1-position of 2-pyrazolin-5-one couplers; $R_{133}$ represents a substituted or unsubstituted anilino group, a substituted or unsubstituted acylamino group (e.g., alkylcarbonamido, phenylcarbonamido, alkoxycarbonamido, phenyloxycarbonamido), a substituted or unsubstituted ureido group (e.g., alkylureido, phenylureido), or a substituted or unsubstituted sulfonamido group; and Z represents a hydrogen atom, a halogen atom (e.g., chlorine, bromine), or a coupling releasable group bonded via an oxygen atom, a nitrogen atom, or a sulfur atom.

In formula (PB), the substituent as represented by Ar includes an alkyl group, a substituted alkyl group (e.g., haloalkyl (e.g., fluoroalkyl), cyanoalkyl, benzylalkyl), a substituted or unsubstituted heterocyclic group (e.g., 4-pyridyl, 2-thiazolyl), and a substituted or unsubstituted aryl group. Substituents for the heterocyclic group or aryl group include an alkyl group (e.g., methyl, ethyl), an alkoxy group (e.g., methoxy, ethoxy), an aryloxy group (e.g., phenyloxy), an alkoxycarbonyl group (e.g., methoxycarbonyl), an acylamino group (e.g., acetylamino), a carbamoyl group, an alkylcarbamoyl group (e.g., methylcarbamoyl, ethylcarbonyl), a dialkylcarbamoyl group (e.g., dimethylcarbamoyl), an arylcarbamoyl group (e.g., phenylcarbamoyl), an alkylsulfonyl group (e.g., methylsulfonyl), an arylsulfonyl group (e.g., phenylsulfonyl), an alkylsulfonamido group (e.g., methanesulfonamido), an arylsulfonamido group (e.g., phenylsulfonamido), a sulfamoyl group, an alkylsulfamoyl group (e.g., ethylsulfamoyl), a dialkylsulfamoyl group (e.g., dimethylsulfamoyl), an alkylthio group (e.g., methylthio), an arylthio group (e.g., phenylthio), a cyano group, a nitro group, and a halogen atom (e.g., fluorine, chlorine, bromine). Two or more substituents, if any, may be the same or different. Preferred of these substituents are a halogen atom, an alkyl group, an alkoxy group, an alkoxycarbonyl group, and a cyano group.

Substituents of the anilino, acylamino, ureido, or sulfonamido group as $R_{133}$ include a halogen atom (e.g., fluorine, chlorine, bromine), a straight chain or branched alkyl group (e.g., methyl, t-butyl, octyl, tetradecyl), an alkoxy group (e.g., methoxy, ethoxy, 2-ethylhexyloxy, tetradecyloxy), an acylamino group (e.g., acetamido, benzamido, butaneamido, octaneamido, tetradecaneamido, α-(2,4-di-t-amylphenoxy)acetamido, α-(2,4-di-t-amylphenoxy)butylamido, α-(3-pentadecylphenoxy)hexaneamido, α-(4-hydroxy-3-t-butylphenoxy)tetradecaneamido, 2-oxo-pyrrolidin-1-yl, 2-oxo-5-tetradecylpyrrolidin- 1-yl, N-methyl-tetradecaneamido), a sulfonamido group (e.g., methanesulfonamido, benzenesulfonamido, ethylsulfonamido, p-toluenesulfonamido, octanesulfonamido, p-dodecylbezenesulfonamido, N-methyl-tetradecanesulfonamido), a sulfamoyl group (e.g., sulfamoyl, N-methylsulfamoyl, N-ethylsulfamoyl, N,N-dimethylsulfamoyl, N,N-dihexylsulfamoyl, N-hexadecylsulfamoyl, N-[3-(dodecyloxy)-propyl]sulfamoyl, N-[4-(2,4-di-t-amylphenoxy)butyl] sulfamoyl, N-methyl-N-tetradecylsulfamoyl), a carbamoyl group (e.g., N-methylcarbamoyl, N-butylcarbamoyl, N-octadecylcarbamoyl, N-[4-(2,4-di-t-amylphenoxy)butyl] carbamoyl, N-methyl-N-tetradecylcarbamoyl), a diacylamino group (e.g., N-succinimido, N-phthalimido, 2,5-dioxo-1-oxazolidinyl, 3-dodecyl-2,5-dioxo- 1-hydantoinyl, 3-(N-acetyl-N-dodecylamino)succinimido), an alkoxycarbonyl group (e.g., methoxycarbonyl, tetradecyloxycarbonyl, benzyloxycarbonyl), an alkoxysulfonyl group. (e.g., methoxysulfonyl, butoxysulfonyl, octyloxysulfonyl, tetradecyloxysulfonyl), an aryloxysulfonyl group (e.g., phenoxysulfonyl, p-methylphenoxysulfonyl, 2,4-di-t-amylphenoxysulfonyl), an alkanesulfonyl group (e.g., methanesulfonyl, ethanesulfonyl, octanesulfonyl, 2-ethylhexylsulfonyl, hexadecanesulfonyl), an arylsulfonyl group (e.g., benzenesulfonyl, 4-nonylbenzenesulfonyl), an alkylthio group (e.g., methylthio, ethylthio, hexylthio, benzylthio, tetradecylthio, 2-(2,4-di-t-amylphenoxy)ethylthio), an arylthio group (e.g., phenylthio, p-tolylthio), an alkyloxycarbonylamino group (e.g., methoxycarbonylamino, ethoxycarbonylamino, benzyloxycarbonylamino, hexadecyloxycarbonylamino), an alkylureido group (e.g., N-methylureido, N,N-dimethylureido, N-methyl-N-dodecylureido, N-hexadecylureido, N,N-dioctadecylureido), an acyl group (e.g., acetyl, benzoyl, octadecanoyl, p-dodecaneamidobenzoyl), a nitro group, a carboxyl group, a sulfo group, a hydroxyl group, and a trichloromethyl group. In these substituents, the alkyl group or moiety has from 1 to 36 carbon atoms, and the aryl moiety has from 6 to 38 carbon atoms.

Examples of the coupling releasable group as represented by Z include those bonded via an oxygen atom, e.g., acetoxy, propanoyloxy, benzoyloxy, ethoxyoxaloyloxy, pyruvinyloxy, cinnamoyloxy, phenoxy, 4-cyanophenoxy, 4-ethanesulfonamidophenoxy, α-naphthoxy, 4-cyanoxy, 4-methanesulfonamidophenoxy, 3-pentadecylphenoxy, benzyloxycarbonyloxy, ethoxy, 2-cyanoethoxy, benzyloxy, 2-phenethyloxy, 2-phenoxyethoxy, 5-phenyltetrazolyloxy, and 2-benzothiazolyloxy; those bonded via a nitrogen atom, such as those described in JP-A-59-99437, e.g., benzenesulfonamido, N-ethyltoluenesulfonamido, heptafluorobutaneamido, 2,3,4,5,6-pentafluorobenzamido, octanesulfonamido, p-cyanophenylureido, N,N-diethylsulfamoylamino, 1-piperidyl, 5,5-dimethyl-2,4-dioxo- 3-oxazolidinyl, 1-benzyl-5-ethoxy-3-hydantoinyl, 2-oxo-1,2-dihydro-1-pyridinyl, imidazolyl, pyrazolyl, 3,5-diethyl-1,2,4-triazol-1-yl, 5- or 6-bromobenzotriazol- 1-yl, 5-methyl-1,2,3,4-triazol-1-yl, and benzimidazolyl; and those bonded via a sulfur atom, e.g., phenylthio, 2-carboxyphenylthio, 2-methoxy-5-octylphenylthio, 4-methanesulfonylphenylthio, 4-octanesulfonamidophenylthio, benzylthio, 2-cyanoethylthio, 5-phenyl- 2,3,4,5-tetrazolylthio, and 2-benzothiazolyl. Preferred of these coupling releasable groups are those bonded via a nitrogen atom, and particularly a pyrazolyl group.

In formula (PA), —E— represents a substituted or unsubstituted alkylene group, a substituted or unsubstituted aralkylene, or a substituted or unsubstituted phenylene group each having up to 10 carbon atoms. The alkylene group may have a straight chain or a branched structure. Examples of the alkylene group include methylene, methylmethylene, dimethylmethylene, dimethylene, trimethylene, tetramethylene, pentamethylene, hexamethylene, and decylmethylene. Examples of the aralkylene group include benzylidene, and examples of the phenylene group include p-phenylene, m-phenylene, and methylphenylene. Substituents for the alkylene, aralkylene or phenylene group as E include an aryl group (e.g., phenyl), a nitro group, a hydroxyl group, a cyano group, a sulfo group, an alkoxy group (e.g., methoxy), an aryloxy group (e.g., phenoxy), an acyloxy group (e.g., acetoxy), an acylamino group (e.g., acetylamino), a sulfonamido group (e.g., methanesulfonamido), a sulfamoyl group (e.g., methylsulfamoyl), a halogen atom (e.g., fluorine, chlorine, bromine), a carboxyl group, a carbamoyl group (e.g., methylcarbamoyl), an alkoxycarbonyl group (e.g., methoxycarbonyl), and a sulfonyl group (e.g., methylsulfonyl). Two or more substituents, if any, may be the same or different.

In the above-described polymer couplers, non-color-forming ethylenically unsaturated monomers incapable of coupling with an oxidation product of an aromatic primary amine developing agent which are copolymerizable with the coupler monomer (PA) include acrylic esters, methacrylic esters, crotonic esters, vinyl esters, maleic diesters, fumaric diesters, itaconic diesters, acrylamides, methacrylamides, vinyl ethers, and styrene or derivatives thereof.

Examples of acrylic esters are methyl acrylate, ethyl acrylate, n-propyl acrylate, isopropyl acrylate, n-butyl acrylate, isobutyl acrylate, t-butyl acrylate, hexyl acrylate, 2-ethylhexyl acrylate, acetoxyethyl acrylate, phenyl acrylate, 2-methoxy acrylate, 2-ethoxy acrylate, and 2-(2-methoxyethoxy)ethyl acrylate. Examples of methacrylic esters are methyl methacrylate, ethyl methacrylate, n-propyl methacrylate, n-butyl methacrylate, t-butyl methacrylate, cyclohexyl methacrylate, 2-hydroxyethyl methacrylate, and 2-ethoxyethyl methacrylate. Examples of crotonic esters are butyl crotonate and hexyl crotonate. Examples of vinyl esters are vinyl acetate, vinyl propionate, vinyl butyrate, vinyl methoxyacetate, and vinyl benzoate. Examples of maleic diesters are diethyl maleate, dimethyl maleate, and dibutyl maleate. Examples of fumaric diesters are diethyl fumarate, dimethyl fumarate, and dibutyl fumarate. Examples of itaconic diesters are diethyl itaconate, dimethyl itaconate, and dibutyl itaconate. Examples of acrylamides are acrylamide, methylacrylamide, ethylacrylamide, propylacrylamide, n-butylacrylamide, t-butylacrylamide, cyclohexylacrylamide, 2-methoxyethylacrylamide, dimethylacrylamide, diethylacrylamide, and phenylacrylamide. Examples of methacrylamides are methylmethacrylamide, ethylmethacrylamide, n-butylmethacrylamide, t-butylmethacrylamide, 2-methoxymethacrylamide, dimethylmethacrylamide, and diethylmethacrylamide. Examples of vinyl ethers are methyl vinyl ether, butyl vinyl ether, hexyl vinyl ether, methoxyethyl vinyl ether, and dimethylaminoethyl vinyl ether. Examples of styrene derivatives are methylstyrene, dimethylstyrene, trimethylstryrene, ethylstyrene, isopropylstyrene, butylstyrene, chloromethylstyrene, methoxystyrene, butoxystyrene, acetoxystyrene, chlorostyrene, dichlorostyrene, bromostyrene, methyl vinylbenzoate, and 2-methylstyrene.

Further included in comonomers are allyl compounds (e.g., allyl acetate), vinyl ketones (e.g., methyl vinyl ketone), vinyl heterocyclic compounds (e.g., vinylpyridine), glycidyl esters (e.g., glycidyl acrylate), unsaturated nitriles (e.g., acrylonitrile), acrylic acid, methacrylic acid, itaconic acid, maleic acid, itaconic monoalkyl esters (e.g., monomethyl itaconate), maleic monoalkyl esters (e.g., monomethyl maleate), citraconic acid, vinylsulfonic acid, acryloyloxyalkylsulfonic acids (e.g., acryloyloxymethylsulfonic acid), and acrylamidoalkylsulfonic acids (e.g., 2-acrylamido- 2-methylethanesulfonic acid). These acids may be in the form of a salt with an alkali metal (e.g., Na, K) or an ammonium ion.

Preferred of the above-mentioned comonomers are acrylic esters, methacrylic esters, styrene or derivatives thereof, maleic esters, acrylamides, and methacrylamides.

These comonomers may be used in combination of two or more thereof. For example, a combination of n-butyl acrylate with styrene or butylstyrene and a combination of t-butyl methacrylate with n-butyl acrylate can be used.

A proportion of the color-forming unit corresponding to the monomer (PB) in the magenta polymer coupler is usually from 5 to 80% by weight. From the standpoint of color reproducibility, color developability, and stability, a preferred proportion is from 30 to 70% by weight. In this case, while not limited, an equivalent molecular weight (gram number of a polymer containing 1 mol of a monomer coupler) usually ranges from about 250 to 4,000.

The polymer coupler which can be used in the present invention is added to a silver halide emulsion layer or a layer adjacent thereto.

Where the magenta polymer coupler is added to a layer containing silver halide, it is added in an amount of from 0,005 to 0.5 mol, and preferably from 0.03 to 0.25 mol, per mol of silver. Where it is added to a light-insensitive layer, the amount to be added is from 0.01 to 1.0 g/m$^2$, and preferably from 0.1 to 0.5 g/m$^2$.

The polymer coupler can be prepared by polymerizing the above-described monomer coupler, dissolving the resulting lipophilic polymer coupler in an organic solvent, and emulsifying the organic solvent solution in a gelatin aqueous solution to form a latex. The polymer coupler may also be prepared directly by emulsion polymerization.

Methods for emulsifying and dispersing a lipophilic polymer coupler in a gelatin aqueous solution to form a latex are described in U.S. Pat. No. 3,451,820, and methods for emulsion polymerization are described in U.S. Pat. Nos. 4,080,211 and 3,370,952 and EP 341,088A2.

Synthesis of the magenta polymer coupler can be carried out by using a polymerization initiator and, as a polymerization solvent, the compound described in JP-A- 56-5543, JP-A-57-94752, JP-A-57-176038, JP-A-57- 204038, JP-A-58-28745, JP-A-58-10738, JP-A-58-42044, and JP-A-58-145944.

The polymerization temperature should be decided in view of the molecular weight of the produced polymer, the kind of an initiator to be used, and the like. Temperatures lower than 0° C. up to 100° C. or even higher are acceptable, but polymerization is usually conducted in temperatures of from 30° to 100° C.

Specific examples of the magenta polymer couplers which can be used in the present invention are shown below for illustrative purposes only but not for limitation. Copolymerization ratios shown are given by mole.

(P-1)
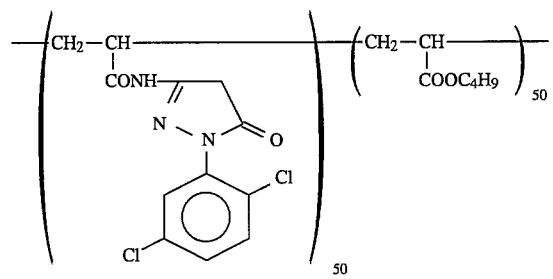
(P-2)
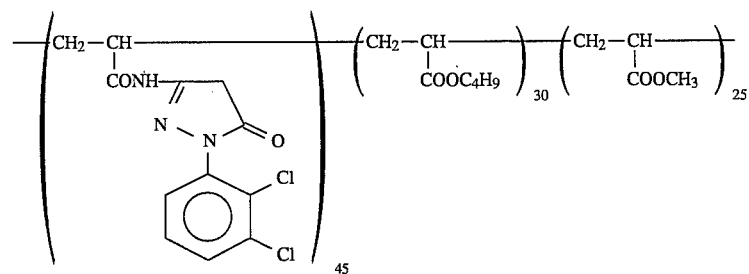
(P-3)
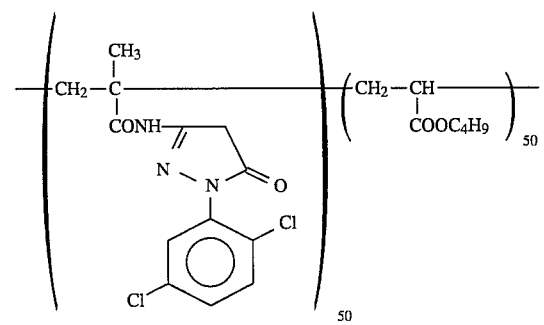
(P-4)
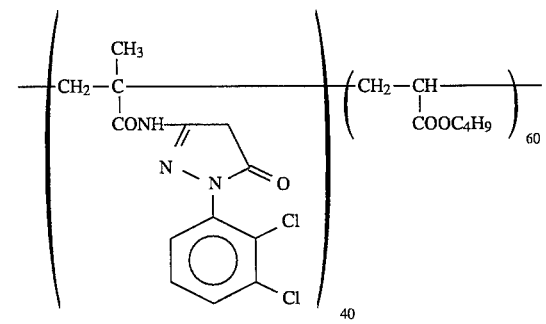

(P-5)
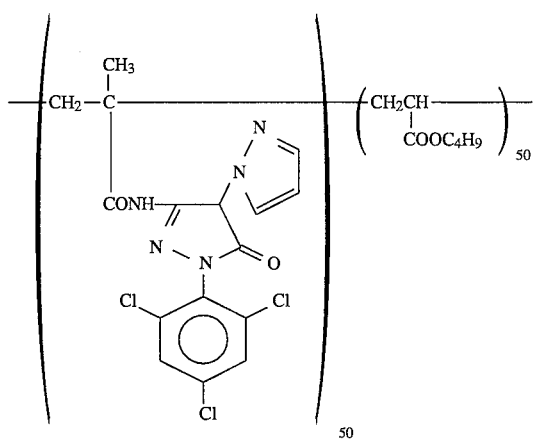
(P-6)
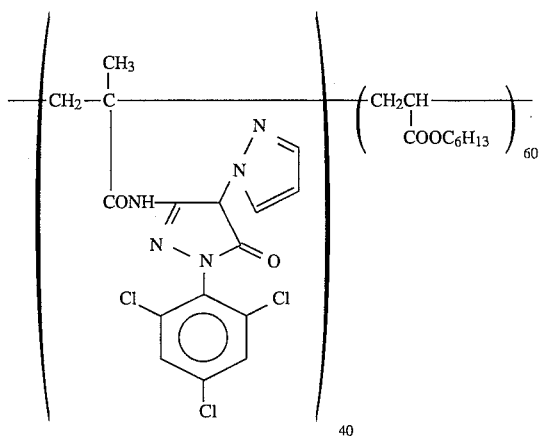
(P-7)
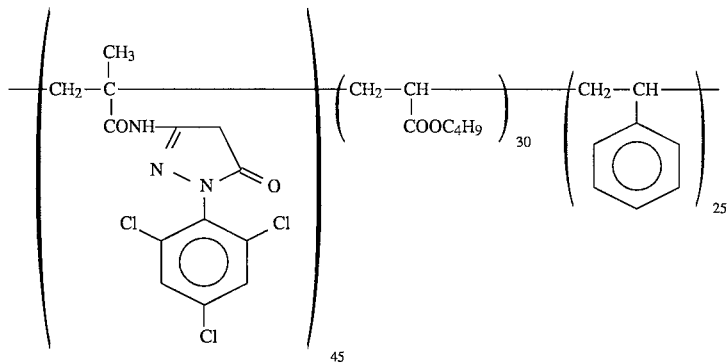

-continued
(P-8)
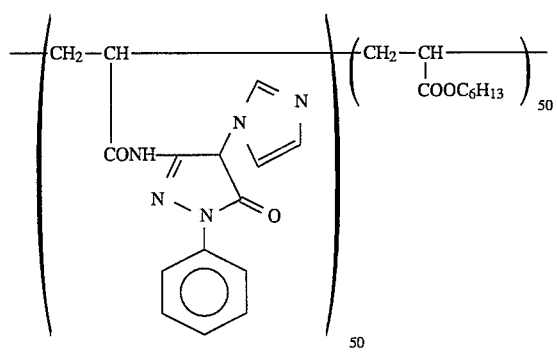
(P-9)
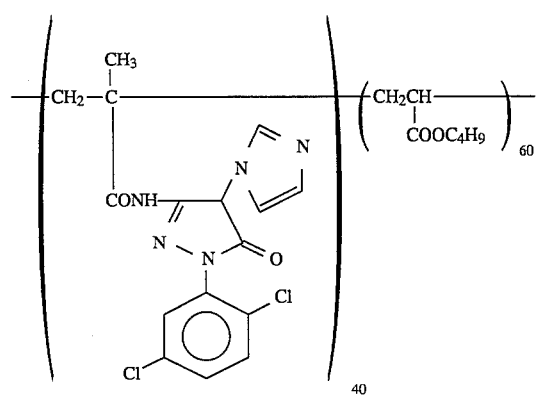
(P-10)
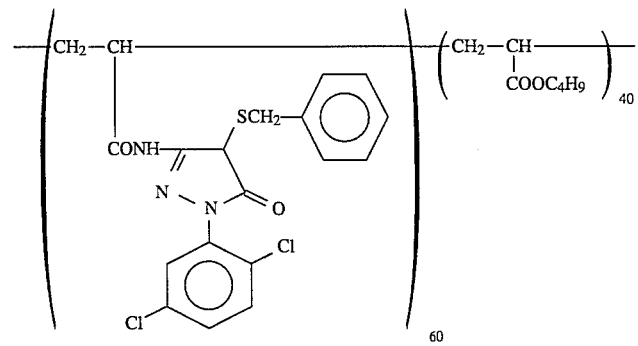

-continued
(P-11)
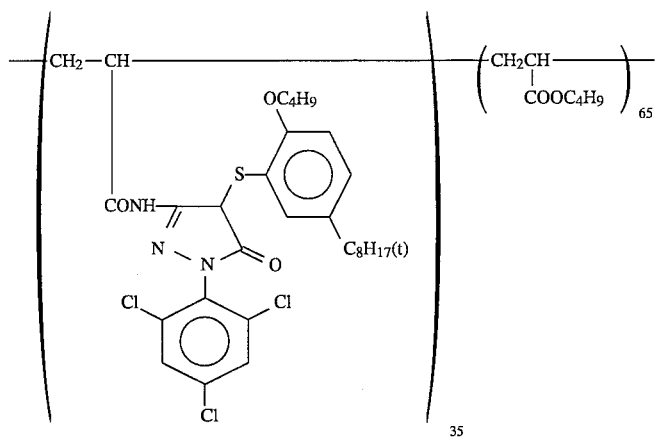
(P-12)
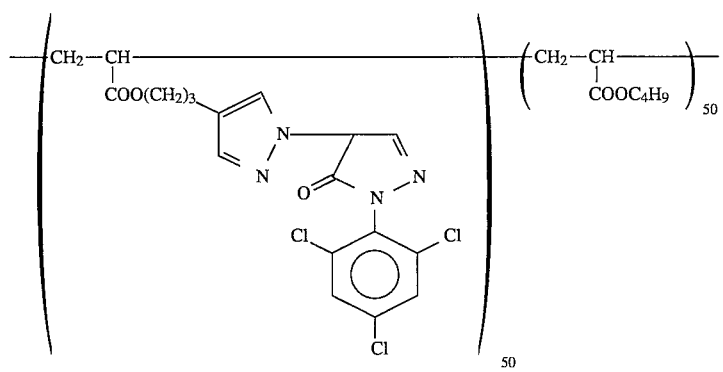
(P-13)
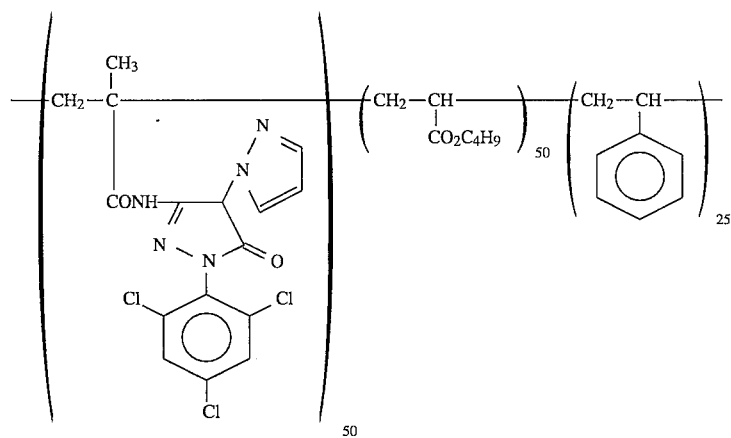

-continued (P-14)

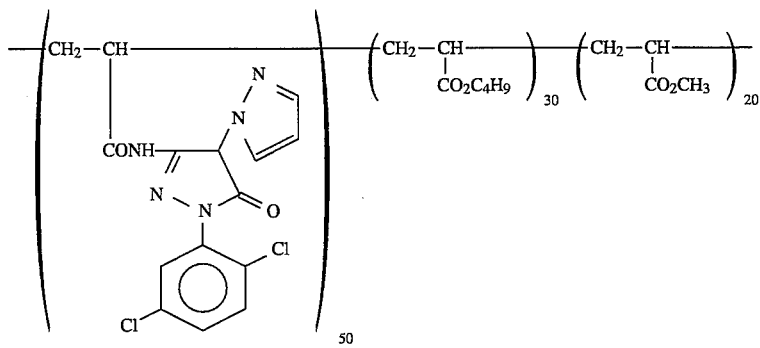

Light-sensitive materials according to the present invention comprise a support having thereon at least one of blue-sensitive, green-sensitive, and red-sensitive silver halide emulsion layers. The number and order of silver halide emulsion layers and light-insensitive layers are not particularly limited. A typical material comprises a support having thereon at least one light-sensitive layer composed of two or more silver halide emulsion layers which have substantially the same color sensitivity to blue light, green light or red light but are different in photosensitivity (hereinafter referred to as unit light-sensitive layer). Multi-layer silver halide color photographic materials generally comprise a support having thereon a red-sensitive unit layer, a green-sensitive unit layer, and a blue-sensitive unit layer in this order. Depending on the end use, the above order of layers may be altered, or two layers having the same color sensitivity may have therebetween a layer having different color sensitivity.

A light-insensitive layer, including various intermediate layers, may be provided between these silver halide light-sensitive layers or as an uppermost or undermost layer.

Such intermediate layers may contain couplers, DIR compounds, etc. as described in JP-A-61-43748, JP-A-59-113438, JP-A-59-113440, JP-A-61-20037, and JP-A-61-20038 and may also contain color mixing inhibitors as usual.

Each unit light-sensitive layer preferably has a two-layer structure composed of a high sensitive emulsion layer and a low sensitive emulsion layer as described in West German Patent 1,121,470 and British Patent 923,045. The two layers of each unit light-sensitive layer are generally provided in a descending order of photosensitivity toward the support. Between the two silver halide emulsion layers, a light-insensitive layer may be provided. It is also possible to provide a low sensitive emulsion layer on the side farther from the support and a high sensitive emulsion layer on the side closer to the support as described in JP-A-57-112751, JP-A-62-200350, JP-A-62-206541, and JP-A- 62-206543.

Specific examples of practical layer orders include an order of low sensitive blue-sensitive layer (BL)/high sensitive blue-sensitive layer (BH)/high sensitive green-sensitive layer (GH)/low sensitive green-sensitive layer (GL)/high sensitive red-sensitive layer (RH)/low sensitive red-sensitive layer (RL)/support, an order of BH/BL/GL/GH/RH/RL/support, and an order of BH/BL/GH/GL/RL/RH/support.

A layer order of blue-sensitive layer/GH/RH/GL/RL/support as described in JP-B-55-34932 and a layer order of blue-sensitive layer/GL/RL/GH/RH/support as described in JP-A-56-25738 and JP-A-62-63936 are also employable.

Further, a unit light-sensitive layer may be composed of three layers whose photosensitivity differs in a descending order toward the support, i.e., the most sensitive silver halide emulsion layer as the upper layer, a middle sensitive silver halide emulsion layer as an intermediate layer, and the least sensitive silver halide emulsion layer as the lower layer, as proposed in JP-B-49-15495. Three layers of different sensitivity in each unit layer may be arranged in the order of middle sensitive emulsion layer/high sensitive emulsion layer/low sensitive emulsion layer from the side farther from a support as described in JP-A-59-202464.

Furthermore, an order of high sensitive emulsion layer/low sensitive emulsion layer/middle sensitive emulsion layer or an order of low sensitive emulsion layer/middle sensitive emulsion layer/high sensitive emulsion layer are also employable.

In the case where a unit layer is composed of 4 or more layers, the layer arrangement can be altered similarly.

As mentioned above, a layer structure or arrangement of light-sensitive materials can be appropriately chosen according to the end use.

Silver halide which can be used in the present invention in addition to the above-described specific silver halide are explained below.

Silver halide used in the photographic emulsion layers is preferably silver iodobromide, silver iodochloride or silver iodochlorobromide each having a silver iodide content of not more than about 30 mol %, and more preferably silver iodobromide or silver iodochlorobromide having a silver iodide content of from about 2 mol % to about 10 mol %.

Silver halide grains of the photographic emulsions may have a regular crystal form, such as a cubic form, an octahedral form, and a tetradecahedral form; an irregular crystal form, such as a spherical form and a plate form; a crystal form having a crystal defect, such as a twinning plane; or a composite crystal form thereof.

Silver halide grains may have a wide range of grain size, including from fine grains of about 0.2 µm or smaller to large grains having a projected area diameter reaching about 10 µm. The silver halide emulsion may be either a mono-dispersed emulsion or a poly-dispersed emulsion.

Silver halide photographic emulsions which are used in the present invention can be prepared by the processes described, e.g., in *Research Disclosure* (hereinafter abbreviated as RD), No. 17643 (Dec., 1978), pp. 22–23, "I. Emulsion Preparation and Types", *ibid*, No. 18716 (Nov., 1979), p. 648, *ibid*, No. 307105 (Nov., 1989), pp. 863–865, P. Glafkides, *Chemic et Phisique Photographique*, Paul Montel (1967), G. F. Duffin, *Photographic Emulsion Chem-* istry, Focal Press (1966), and V. L. Zelikman et al., *Making and Coating Photographic Emulsion,* Focal Press (1964).

Mono-dispersed emulsions described in U.S. Pat. Nos. 3,574,628 and 3,655,394 and British Patent 1,413,748 are preferably used as well.

Tabular grains having an aspect ratio of about 3 or more are also useful. Such tabular grains can easily be prepared by the processes described, e.g., in Gutoff, *Photographic Science and Engineering,* Vol. 14, pp. 248– 257 (1970) , U.S. Pat. Nos. 4,434,226, 4,414,310, 4,433,048, and 4,439,520, and British Patent 2,112,157.

The silver halide grains may be homogeneous grains having a uniform crystal structure throughout the individual grains or heterogeneous grains including those in which the inside and the outer shell have different halogen compositions, those in which the halogen composition differs among layers, and those having fused thereto silver halide of different halogen composition through epitaxy. Silver halide grains fused with compounds other than silver halides, e.g., silver rhodanide or lead oxide may also be used. A mixture comprising grains of various crystal forms is employable.

The photographic emulsions may be either of surface latent image type which forms a latent image predominantly on the surface of grains or of internal latent image type which forms a latent image predominantly in the inside of the grains but should be of negative type. Internal latent image type emulsions may be of core/shell type as described in JP-A-63- 264740. The core/shell type internal latent image type emulsions can be prepared by the process described n JP-A- 59-133542. The thickness of the shell of this type of emulsion preferably ranges from 3 to 40 nm, and particularly from 5 to 20 nm, though varying depending on the developing processing.

Silver halide emulsions are usually subjected to physical ripening, chemical ripening, and spectral sensitization. Additives which can be used in these steps are described in *RD,* Nos. 17643, 18716, and 307105 as hereinafter listed.

In the light-sensitive material of the present invention, a mixture of two or more light-sensitive emulsions differing in at least one of characteristics including grain size, grain size distribution, halogen composition, crystal form, and sensitivity can be used in the same layer.

Surface-fogged silver halide grains as described in U.S. Pat. No. 4,082,553, inside-fogged silver halide grains as described in U.S. Pat. No. 4,626,498 and JP-A- 59-214852, and colloidal silver can be preferably used in light-sensitive silver halide emulsion layers and/or substantially light-insensitive hydrophilic colloidal layers. The terminology "inside- or surface-fogged silver halide grains" as used herein means silver halide grains which are evenly (non-imagewise) developable, exposed or unexposed, without distinction. Methods for preparing inside- or surface-fogged silver halide grains are described in U.S. Pat. No. 4,626,498 and JP-A-59- 214852.

In the inside-fogged core/shell type silver halide grains, the core and the outer shell may have either the same or different halogen composition.

The inside- or surface-fogged silver halide grains may have any halogen composition selected from silver chloride, silver chlorobromide, silver iodobromide, and silver chloroiodobromide. While these fogged silver halide grains are not particularly limited in grain size, a preferred mean grain size is from 0.01 to 0.75 µm, and particularly from 0.05 to 0.6 µm. The fogged silver halide grains are not particularly limited in crystal form, either regular or irregular. A poly-dispersed emulsion can be used, but a mono-dispersed emulsion in which at least 95% of the total weight or number of silver halide grains have a grain size falling within 40% of a mean grain size) is preferred.

In the present invention, light-insensitive silver halide fine grains are preferably used. The terminology "light-insensitive silver halide fine grains" as used herein means silver halide fine grains which are not sensitive to light of imagewise exposure for obtaining a color image and are therefore not substantially developed during development processing. It is preferable that the light-insensitive silver halide fine grains are not previously fogged.

The silver halide fine grains have a silver bromide content of from 0 to 100 mol % and may contain, if desired, silver chloride and/or silver iodide, and preferably have a silver iodide content of from 0.5 to 10 mol %.

The silver halide fine grains preferably have a mean grain size (an average circle-equivalent diameter of the projected area) of from 0.01 to 0.5 µm, and more preferably from 0.02 to 0.2 µm.

The silver halide fine grains can be prepared in the same manner as for general light-sensitive silver halide grains. The surface of silver halide fine grains formed needs to be neither optically sensitized nor spectrally sensitized. It is desirable, however, that a known stabilizer, such as triazole compounds, azaindene compounds, benzothiazolium compounds, mercapto compounds, and zinc compounds, be added before the silver halide fine grains are added to a coating composition. The layer containing the silver halide fine grains preferably contains colloidal silver.

The light-sensitive material of the present invention preferably has a silver coverage of not more than 6.0 g/m$^2$, and more preferably not more than 4.5 g/m$^2$.

Known photographic additives which can be used in the present invention are described in *RD,* Nos. 17643, 18716, and 307105 supra as tabulated below.

| Additive | RD 17643 | RD 18716 | RD 307105 |
| --- | --- | --- | --- |
| 1. Chemical Sensitizer | p. 23 | p. 648, right column (RC) | p. 866 |
| 2. Sensitivity Increasing Agent | | p. 648, right column (RC) | |
| 3. Spectral Sensitizer, Supersensitizer | pp. 23–24 | p. 648, RC to p. 649, RC | pp. 866–868 |
| 4. Brightening Agent | p. 24 | p. 647, RC | p. 868 |
| 5. Antifoggant, Stabilizer | pp. 24–25 | p. 649, RC | pp. 868–870 |
| 6. Light Absorber, Filter Dye, Ultrasonic Absorber | pp. 25–26 | p. 649, RC to P. 650, left column (LC) | p. 873 |
| 7. Stain Inhibitor | p. 25, RC | P. 650, LC to RC | p. 872 |
| 8. Dye Image Stabilizer | p. 25 | p. 650, LC | " |
| 9. Hardening Agent | p. 26 | p. 651, LC | pp. 874–875 |
| 10. Binder | p. 26 | " | pp. 873–874 |
| 11. Plasticizer, Lubricant | p. 27 | P. 650, RC | p. 876 |
| 12. Coating Aid, Surface Active Agent | pp. 26–27 | p. 650, RC | pp. 875–876 |
| 13. Antistatic Agent | p. 27 | " | pp. 876–877 |
| 14. Matting Agent | | | pp. 878–879 |

In order to prevent deterioration in photographic performance due to formaldehyde gas, a compound capable of reacting with formaldehyde to fix it as described in U.S. Pat. Nos. 4,411,987 and 4,435,503 is preferably added to light-sensitive materials.

The light-sensitive material of the invention preferably contains the mercapto compound described in U.S. Pat. Nos. 4,740,454 and 4,788,132, JP-A-62-18539, and JP-A-1-283551.

The light-sensitive material preferably contains a compound capable of releasing a fogging agent, a development accelerator, or a silver halide solvent, or a precursor thereof regardless of a developed silver amount produced by development processing, as described in JP-A-1-106052.

The light-sensitive material preferably contains the dye dispersion described in WO 88/04794 and JP-A-1- 502912 or the dye described in EP 317,308A, U.S. Pat. No. 4,420, 555 and JP-A-1-259358.

Various couplers can be used in the present invention. Specific examples of useful couplers are described in patents cited in RD, No. 17643, VII-C to G and RD, No. 307105, VII-C to G.

Examples of suitable yellow couplers are described, e.g., in U.S. Pat. Nos. 3,933,501, 4,022,620, 4,326,024, 4,401, 752, and 4,248,961, JP-B-58-10739, British Patents 1,425, 020 and 1,476,760, U.S. Pat. Nos. 3,973,968, 4,314,023, and 4,511,649, and EP 249,473A.

Examples of suitable magenta couplers include 5-pyrazolone couplers and pyrazoloazole couplers. Examples of particularly preferred magenta couplers are described in U.S. Pat. Nos. 4,310,619 and 4,351,897, European Patent 73,636, U.S. Pat. Nos. 3,061,432 and 3,725,067, RD No. 24220 (Jun., 1984), JP-A-60-33552, RD No. 24230 (Jun., 1984), JP-A-60-43659, JP-A-61-72238, JP-A-60-35730, JP-A-55-118034, JP-A-60-185951, U.S. Pat. Nos. 4,500, 630, 4,540,654, and 4,556,630, and WO 88/04795.

Cyan couplers include phenol couplers and naphthol couplers. Examples of suitable couplers are described in U.S. Pat. Nos. 4,052,212, 4,146,396, 4,228,233, 4,296,200, 2,369,929, 2,801,171, 2,772,162, 2,895,826, 3,772,002, 3,758,308, 4,334,011, and 4,327,173, West German Patent Publication No. 3,329,729, EP 121,365A, EP 249,453A, U.S. Pat. Nos. 3,446,622, 4,333,999, 4,775,616, 4,451,559, 4,427,767, 4,690,889, 4,254,212, and 4,296,199, and JP-A-61-42658.

Typical examples of polymerized dye-forming couplers are described in U.S. Pat. Nos. 3,451,820, 4,080,211, 4,367, 282, 4,409,320, and 4,576,910, British Patent 2,102,137, and EP 341,188A.

Examples of suitable couplers which develop a dye having moderate diffusibility are described in U.S. Pat. No. 4,366,237, British Patent 2,125,570, European Patent 96,570, and West German Patent (OLS) No. 3,234,533.

Examples of suitable colored couplers which can be used for correcting unnecessary absorption of a developed dye are described in RD, No. 17643, VII-G, ibid, No. 307105, VII-G, U.S. Pat. No. 4,163,670, JP-B-57- 39413, U.S. Pat. Nos. 4,004,929 and 4,138,258 and British Patent 1,146,368. Further, couplers capable of releasing a fluorescent dye upon coupling with which unnecessary absorption of a developed dye is corrected as described in U.S. Pat. No. 4,774,181 and couplers having a dye precursor group as a releasable group which is capable of reacting with a developing agent to form a dye as described in U.S. Pat. No. 4,777,120 are preferably used.

Couplers capable of releasing a photographically useful residue on coupling are also used to advantage. Examples of suitable DIR couplers capable of releasing a development inhibitor other than those represented by formula (I) are described in patents cited in RD, No. 17643, VII-F and ibid, No. 307105, VII-F, JP-A-57- 151944, JP-A-57-154234, JP-A-60-184248, JP-A-63-37346, JP-A-63-37350, and U.S. Pat. Nos. 4,248,962 and 4,782,012.

Examples of suitable couplers which imagewise release a nucleating agent or a development accelerator at the time of development are described in British Patents 2,097,140 and 2,131,188, JP-A-59-157638, and JP-A- 59-170840. Compounds capable of releasing a fogging agent, a development accelerator, a silver halide solvent, etc. on oxidation-reduction reaction with an oxidation product of a developing agent as described in JP-A-60-107029, JP-A-60-252340, and JP-A-1-44940 are also preferably used.

Additional examples of couplers which can be used in the light-sensitive material of the present invention include competing couplers as described in U.S. Pat. No. 4,130,427; polyequivalent couplers as described in U.S. Pat. Nos. 4,283,472, 4,338,393, and 4,310,618; couplers capable of releasing a DIR redox compound, couplers capable of releasing a DIR coupler, redox compounds capable of releasing a DIR coupler, or redox compounds capable of releasing a DIR redox compound as described in JP-A-60-185950 and JP-A-62- 24252; couplers capable of releasing a dye which restores its color after release as described in EP 173,302A and EP 313,308A; couplers capable of releasing a bleaching accelerator as described in RD, Nos. 11449 and 24241 and JP-A-61-201247; couplers capable of releasing a ligand as described in U.S. Pat. No. 4,555,477; couplers capable of releasing a leuco dye as described in JP-A-63-75747; and couplers capable of releasing a fluorescent dye as described in U.S. Pat. No. 4,774,181.

These couplers are introduced into photographic materials by various known dispersion methods. High-boiling organic solvents which are useful in an oil-in-water dispersion method are described, e.g., in U.S. Pat. No. 2,322,027. Specific examples of the high-boiling organic solvents having a boiling point of 175° C. or higher under atmospheric pressure are phthalic esters (e.g., dibutyl phthalate, dicyclohexyl phthalate, di-2-ethylhexyl phthalate, decyl phthalate, bis(2,4-di-t-amylphenyl)phthalate, bis(2,4-di-t-amylphenyl) isophthalate, bis(1,1-diethylpropyl)phthalate), phosphoric or phosphonic esters (e.g., triphenyl phosphate, tricresyl phosphate, 2-ethylhexyldiphenyl phosphate, tricyclohexyl phosphate, tri-2-ethylhexyl phosphate, tridodecyl phosphate, tributoxyethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecanamide, N,N-diethyllaurylamide, N-tetradecylpyrrolidone), alcohols or phenols (e.g., isostearyl alcohol, 2,4-di-t-amylphenol), aliphatic carboxylic acid esters (e.g., bis( 2-ethylhexyl) sebacate, dioctyl azelate, glycerol tributyrate, isostearyl lactate, trioctyl citrate), aniline derivatives (e.g., N,N-dibutyl-2-butoxy-5-t-octylaniline), and hydrocarbons (e.g., paraffin, dodecylbenzene, diisopropylnaphthalane). Organic solvents having a boiling point of not lower than about 30° C., and preferably from 50° C. to about 160° C. may be used in combination as an auxiliary solvent. Typical examples of such an auxiliary solvent are ethyl acetate, butyl acetate, ethyl propionate, methyl ethyl ketone, cyclohexanone, 2-ethoxyethyl acetate, and dimethylformamide.

With respect to a latex dispersion method, the steps involved, the effects, and specific examples of loadable latices are described in U.S. Pat. No. 4,199,363 and West German Patent (OLS) Nos. 2,541,274 and 2,541,230.

The color light-sensitive materials of the present invention preferably contain various antiseptics or antifungal agents, such as phenethyl alcohol; and 1,2-benzisothiazolin-3-one, n-butyl p-hydroxybenzoate, phenol, 4-chloro-3,5-dimethylphenol, 2-phenoxyethanol, 2-(4-thiazolyl)benzimidazole, etc. as described in JP-A- 63-257747, JP-A-62-272248, and JP-A-1-80941.

The present invention can be applied to a wide variety of color light-sensitive materials, for example, color negative films for general use or for movies, color reversal films for slides or TV, color papers, color positive films, and color reversal papers.

Examples of supports which can be suitably used in the color light-sensitive materials are described, e.g., in *RD*, No. 17643, p. 28, *ibid*, No. 18716, pp. 647 (right column) to 648 (left column), and *ibid*, No. 307105, p. 879.

In the color light-sensitive materials of the present invention, the hydrophilic colloidal layers on the side having emulsion layers preferably have a total film thickness of not more than 28 μm, more preferably not more than 23 μm, most preferably not more than 18 μm, and particularly not more than 16 μm, and a rate of swelling $T_{1/2}$ of not more than 30 seconds, and more preferably not more than 20 seconds. The terminology "total film thickness" as used herein means a film thickness as measured after conditioning at 25° C. and a relative humidity of 55% for 2 days. The terminology "rate of swelling $T_{1/2}$" means a time required for a color light-sensitive material to be swollen to ½ the saturated swollen thickness, the saturated swollen thickness being defined to be 90% of the maximum swollen thickness which is reached when the color light-sensitive material is swollen with a color developing solution at 30° C. for 3 minutes and 15 seconds. The rate of swelling can be determined by methods known in the art using, for example, a swellometer of the type described in A. Green, et al., *Photographic Science and Engineering*, Vol. 19, No. 2, pp. 124–129.

The rate of swelling $T_{1/2}$ can be controlled by adding a proper amount of a hardening agent for a gelatin binder or by varying aging conditions after coating.

Further, the light-sensitive material preferably has a degree of swelling of from 150 to 400%. The terminology "degree of swelling" as used herein means a value obtained from the maximum swollen film thickness as defined above according to formula: (maximum swollen film thickness–film thickness)/film thickness.

The light-sensitive material of the present invention preferably has a hydrophilic colloidal layer(s) called backing layer(s) having a total dry thickness of from 2 to 20 μm on the side opposite to the emulsion layer side. The backing layers preferably contain the above-described additives, e.g., light absorbents, filter dyes, ultraviolet absorbents, antistatic agents, hardening agents, binders, plasticizers, lubricants, coating aids, and surface active agents. The backing layers preferably have a degree of swelling of from 150 to 500%.

The above-described color photographic materials can be development processed according to usual methods as described in *RD*, No. 17643, pp. 28–29, *ibid*, No. 18716, p. 615, left to right columns, and *ibid*, No. 307105, pp. 880–881.

A color developing solution to be used for development processing is preferably an alkaline aqueous solution containing an aromatic primary amine color developing agent. Useful color developing agents include aminophenol compounds and preferably p-phenylenediamine compounds. Typical examples of p-phenylenediamine compounds are 3-methyl-4-amino-N,N-diethylaniline, 3-methyl-4-amino-N-ethyl-N-β-hydroxyethylaniline, 3-methyl-4-amino-N-ethyl-N-β-methanesulfonamidoethylaniline, 3-methyl-4-amino-N-ethyl-β-methoxyethylaniline, and salts thereof (e.g., sulfates, hydrochlorides, and p-toluenesulfonates), with 3-methyl-4-amino-N-ethyl-N-β-hydroxyethylaniline sulfate being particularly preferred. These developing agents may be used either individually or in combination of two or more thereof according to the purpose.

The color developing solution usually contains pH buffering agents, e.g., carbonates, borates or phosphates of alkali metals, and development inhibitors or antifoggants, e.g., chlorides, bromides, iodides, benzimidazoles, benzothiazoles, and mercapto compounds. If desired, the color developing solution further contains various preservatives, such as hydroxylamine, diethylhydroxylamine, sulfites, hydrazines (e.g., N,N-biscarboxymethylhydrazine), phenyl semicarbazides, triethanolamine, and catecholsulfonic acids; organic solvents, e.g., ethylene glycol and diethylene glycol; development accelerators, e.g., benzyl alcohol, polyethylene glycol, quaternary ammonium salts, and amines; dye-forming couplers; competing couplers; auxiliary developing agents (e.g., 1-phenyl-3-pyrazolidone); viscosity-imparting agents; and various chelating agents, such as aminopolycarboxylic acids, aminopolyphosphonic acids, alkylphosphonic acids, and phosphonocarboxylic acids (e.g., ethylenediaminetetraacetic acid, nitrilotriacetic acid, ethylenetriaminepentaacetic acid, cyclohexanediaminetetraacetic acid, hydroxyethyliminodiacetic acid, 1-hydroxyethylidene-1,1-diphosphonic acid, nitrilo-N,N,N-trimethylenephosphonic acid, ethylenediamine-N,N,N,N-tetramethylenephosphonic acid, ethylenediamine-di(o-hydroxyphenylacetic acid, and salts thereof).

In case of carrying out reversal processing, color development is generally preceded by black-and-white (hereinafter abbreviated as B/W) development. A B/W developing solution to be used for B/W development contains one or more of known B/W developing agents, such as dihydroxybenzenes (e.g., hydroquinone), 3-pyrazolidones (e.g., 1-phenyl-3-pyrazolidone), and aminophenols (e.g., N-methyl-p-aminophenol).

The color or B/W developing solution generally has a pH between 9 and 12. A rate of replenishment for these developing solutions, though varying depending on the kind of color photographic material to be processed, is usually not more than 3 l per $m^2$ of a light-sensitive material. The rate of replenishment can be reduced to 500 ml/$m^2$ or less by reducing a bromide ion concentration in the replenisher. When processing is carried out at a reduced rate of replenishment, it is desirable to prevent evaporation and aerial oxidation of a processing solution by minimizing a contact area of the processing solution with air.

The contact area between a photographic processing solution and air can be expressed in terms of opening ratio calculated by dividing a contact area ($cm^2$) of the processing solution with air by a volume ($cm^3$) of the processing solution. The opening ratio as defined above is preferably not more than 0.1, and more preferably between 0,001 and 0.05.

The opening ratio of the processing tank can be so adjusted by, for example, putting a barrier, such as a floating cover, on the liquid surface, using a movable cover as described in JP-A-1-82033, or utilizing slit development processing as described in JP-A-63-216050.

Reduction of the opening ratio is preferably applied to not only color development and B/W development but also all the subsequent steps, such as bleach, blix, fixing, washing, and stabilization.

Reduction of a replenishment rate may also be achieved by using a means for suppressing accumulation of a bromide ion in the developing solution.

A processing time with the color developing solution is from 2 to 5 minutes. The processing time may be shortened by conducting development processing at an elevated temperature and an increased pH in an increased concentration of the color developing agent.

The photographic emulsion layers after color development are usually subjected to bleach. Bleach and fixing may be carried out either simultaneously (blix) or separately. For rapid processing, bleach may be followed by blix. Further, the mode of desilvering can be arbitrarily selected according to the end use. For example, blix may be effected using two tanks connected, or fixing may be followed by blix, or blix may be followed by bleach.

Bleaching agents to be used include compounds of polyvalent metals, e.g., iron (III), peracids, quinones, and nitroso compounds. Typical bleaching agents include organic complex salts of iron (III), e.g., complex salts with aminopolycarboxylic acids (e.g., ethylenediaminetetraacetic acid, diethylenetriaminepentaacetic acid, cyclohexanediaminetetraacetic acid, methyliminodiacetic acid, 1,3-diaminopropanoltetraacetic acid, glycol ether diaminetetraacetic acid), citric acid, tartaric acid, or malic acid. Preferred of them are aminopolycarboxylic acid iron (III) complexes, e.g., (ethylenediaminetetraacetato)iron (III) salts and (1,3-diaminopropanetetraacetato)iron (III) salts, from the standpoint of rapidness of processing and prevention of environmental pollution. Aminopolycarboxylic acid iron (III) complex salts are particularly useful either in a bleaching bath or in a blix monobath. A bleaching bath or blix bath containing these aminopolycarboxylic acid iron (III) complex salts usually has a pH between 4.0 and 8.0. A lower pH is also employed for rapid processing.

If desired, a fixing bath, a blix bath, or a prebath thereof may contain known bleaching accelerators. Useful bleaching accelerators include compounds having a mercapto group or a disulfide group as described in U.S. Pat. No. 3,893,858, German Patents 1,290,812 and 2,059,988, JP-A-53-32736, JP-A-53-57831, JP-A-53-37418, JP-A-53-72623, JP-A-53-95630, JP-A-53- 95631, JP-A-53-104232, JP-A-53-124424, JP-A-53-141623, JP-A-53-28426, and RD, No. 17129 (Jul., 1978); thiazolidine derivatives as described in JP-A-50-140129; thiourea derivatives as described in JP-B-45-8506, JP-A- 52-20832, JP-A-53-32735, and U.S. Pat. No. 3,706,561; iodides as described in West German Patent 1,127,715 and JP-A-58-16235; polyoxyethylene compounds as described in German Patents 966,410 and 2,748,430; polyamine compounds described in JP-B-45-8836; compounds described in JP-A-49-40943, JP-A-49-59644, JP-A-53-94927, JP-A-54- 35727, JP-A-55-26506, and JP-A-58-163940; and a bromide ion. Among them, compounds having a mercapto group or a disulfide group are preferred because of their high accelerating effect. The compounds disclosed in U.S. Pat. No. 3,893,858, West German Patent 1,290,812, and JP-A- 53-95630 are particularly preferred. In addition, the compounds disclosed in U.S. Pat. No. 4,552,834 are also preferred. These bleaching accelerators may be incorporated into a light-sensitive material. The bleaching accelerators are particularly effective for blix of color light-sensitive materials used in camera.

For the purpose of preventing bleach stain, the bleaching or blix bath preferably contains organic acids. Particularly preferred organic acids used to this effect are those having an acid dissociation constant (pKa) of from 2 to 5, e.g., acetic acid and propionic acid.

Fixing agents which can be used in a fixing or blix bath include thiosulfates, thiocyanates, thioether compounds, thioureas, and a large quantity of an iodide, with thiosulfates being commonly employed. In particular, ammonium thiosulfate is widely useful. A combined use of a thiosulfate and a thiocyanate, a thioether compound, a thiourea, etc. is also preferred. Preservatives for the fixing or blix bath preferably include sulfites, bisulfites, carbonyl-bisulfite adducts, and sulfinic acid compounds described in EP 294769A.

The fixing or blix bath preferably contains various aminopolycarboxylic acids or organophosphonic acids for stabilization.

Further, the fixing or blix bath preferably contains 0.1 to 10 mol/l of compounds having a pKa of from 6.0 to 9.0 for pH adjustment, preferably imidazoles, e.g., imidazole, 1-methylimidazole, 1-ethylimidazole, and 2-methylimidazole.

The total time of desilvering is preferably as short as possible as long as insufficient desilvering does not result. A preferred desilvering time is from 1 to 3 minutes, and more preferably from 1 to 2 minutes. The desilvering temperature is from 25° to 50° C., and preferably from 35° to 45° C. In the preferred temperature range, the rate of desilvering is improved, and stain formation after processing is effectively prevented.

It is desirable that desilvering should be performed while reinforcing stirring as much as possible. Methods or means for achieving reinforced stirring include a method in which a jet stream of a processing solution is made to strike against the surface of the emulsion layer as described in JP-A-62-183460; a method of using a rotating means to enhance stirring effects as described in JP-A-62-183461; a method in which a light-sensitive material is moved with its emulsion surface being in contact with a wire blade placed in a processing solution to make turbulence; and a method of increasing a total flow of a circulating processing solution. These stirring means are effective in any of a bleaching bath, a blix bath and a fixing bath. Reinforced stirring appears to accelerate supply of a bleaching agent or a fixing agent to emulsion layers and, as a result, to increase the rate of desilvering.

The above-described means for reinforced stirring is more effective in the case where a bleaching accelerator is used, markedly enhancing acceleration effects and eliminating the fixing inhibitory effect of the bleaching accelerator.

An automatic developing machine which can be used for processing the light-sensitive material preferably has a means for carrying a light-sensitive material as described in JP-A-60-191257, JP-A-60-191258, and JP-A-60-191259. As mentioned in JP-A-60-191257 supra, such a carrying means is highly effective to considerably reduce carry-over of a processing solution from a prebath into a succeeding bath thereby to prevent reduction of processing capacity. This means is particularly effective for reduction of processing time or replenishment rate in each processing step.

The silver halide color light-sensitive material after desilvering is generally subjected to washing and/or stabilization.

The amount of washing water to be used in the washing step is selected from a broad range depending on characteristics of the light-sensitive material (e.g., the kind of photographic materials such as couplers), the end use of the light-sensitive material, the temperature of washing water, the number of washing tanks (the number of stages), the replenishing system (e.g., counter-flow system or direct-flow system), and other various conditions. For example, a relation between the number of washing tanks and the quantity of water in a multi-stage counter-flow system can be obtained by the method described in *Journal of the Society of Motion Picture and Television Engineers,* Vol. 64, pp. 248–253 (May, 1955).

According to the disclosed multi-stage counter-flow system, a requisite amount of water can be greatly reduced. On the other hand, bacteria tend to grow in the tank with an increase in water retention time, and suspended bacterial cells adhere to light-sensitive materials. Such a problem can be effectively coped with by adopting a method of reducing calcium and magnesium ions of washing water as described in JP-A-62-288838. It is also effective to use bactericides, such as isothiazolone compounds or thiabendazole compounds as described in JP-A-57-8542; chlorine type bactericides, e.g., chlorinated sodium isocyanurate; and other bactericides described in Horiguchi Hiroshi, *Bokin bobaizai no kagaku,* Sankyo Shuppan (1986), Eisei Gijutsukai (ed.), *Biseibutsu no mekkin, sakkin, bobai gijutsu* Kogyo Gijutsukai (1982), and Nippon Bokin Bobai Gakkai (ed.), *Bokin bobaizai jiten* (1986), e.g., benzotriazole.

Washing water has a pH usually between 4 and 9, and preferably between 5 and 8. Washing conditions, though varying depending on the characteristics or the end use of the light-sensitive material and the like, are usually from 15° to 45° C. in temperature and from 20 seconds to 10 minutes in time, and preferably from 25° to 40° C. in temperature and from 30 seconds to 5 minutes in time.

The washing step may be followed by stabilization processing. Where stabilization is conducted in place of washing, any of known stabilizing techniques described, e.g., in JP-A-57-8543, JP-A-58-14834, and JP-A-60-220345 can be utilized. Where washing is followed by stabilization, a stabilizing bath to be used includes a solution containing a dye stabilizer and a surface active agent, which is used as a final bath for color light-sensitive materials for shooting. Suitable dye stabilizers include aldehydes, e.g., formalin and glutaraldehyde, N-methylol compounds, hexamethylenetetramine, and an aldehyde-sulfite adduct. If desired, the stabilizing bath may also contain various chelating agents and antifungal agents.

An overflow accompanying replenishment for washing and/or stabilization may be reused in other processing steps, such as a desilvering step.

In cases where each processing solution is concentrated by vaporization during processing with an automatic developing machine, water is preferably supplied to the processing solution for correction of concentration.

For the purpose of simplifying and speeding up processing, the silver halide color light-sensitive material may contain therein a color developing agent, preferably in the form of a precursor thereof. Examples of color developing agent precursors include indoaniline compounds described in U.S. Pat. No. 3,342,597, Schiff base compounds described in U.S. Pat. No. 3,342,599 and *RD*, Nos. 14850 and 15159, aldol compounds described in *RD*, No. 13924, metal complex salts described in U.S. Pat. No. 3,719,492, and urethane compounds described in JP-A-53- 135628.

If desired, the silver halide color light-sensitive material may further contain therein various 1-phenyl- 3-pyrazolidone compounds for the purpose of accelerating color development. Typical examples of these accelerators are described in JP-A-56-64339, JP-A- 57-144547, and JP-A-58-115438.

Each of the above-described processing solutions is used at a temperature of from 10° to 50° C. and, in a standard manner, from 33° to 38° C. Higher processing temperatures may be employed for reducing processing time, or lower temperatures may be employed for improving image quality or stability of the processing solution.

The prevent invention is also applicable to heat-developable light-sensitive materials described in U.S. Pat. No. 4,500,626, JP-A-60-133449, JP-A-59-218443, JP-A-61-238056, and EP 210,660A2.

The present invention is now illustrated in greater detail by way of the following Examples, but it should be understood that the present invention is not deemed to be limited thereto. All the percents and ratios are by weight unless otherwise indicated.

EXAMPLE 1

Preparation of Emulsions

In 800 ml of distilled water were dissolved 20 g of inert gelatin, 2.4 g of potassium bromide, and 2.05 g of potassium iodide, and the solution was kept at 58° C. with stirring. To the solution was added instantaneously 150 cc of an aqueous solution containing 5.0 g of silver nitrate, and excess potassium bromide was further added thereto, followed by allowing the mixture to undergo physical ripening for 20 minutes. To the resulting emulsion were added silver nitrate aqueous solutions having a concentration of 0.2 mol/l, 0.67 mol/l, and 2 mol/l and a mixed aqueous solution containing 58 mol % of potassium bromide and 42 mol % of potassium iodide each at a rate of 10 cc/min according to the method described in U.S. Pat. No. 4,242,445 to allow silver iodobromide grains having an iodide content of 42 mol % to grow. After washing for desalting, there was obtained 900 g of a silver iodobromide emulsion having a mean grain size of 0.61 μm. The resulting emulsion was designated Emulsion a.

In the same manner as for Emulsion a, Emulsions b, c, d, and e each having a silver iodide content of 42 mol % and a mean grain size of 0.59 μm, 0.56 μm, 0.52 μm, and 0.46 μm, respectively, were prepared.

To 300 g of Emulsion a were added 850 cc of distilled water and 30 cc of a 10% aqueous potassium bromide solution, and the solution was heated to 70° C. To the solution was added 0.02 g of Compound (18) of formula (A) while stirring, 30 cc of an aqueous solution containing 33 g of silver nitrate and 320 cc of an aqueous solution containing 25 g of potassium bromide were added thereto simultaneously over 40 minutes while maintaining a pAg at 8.0, and then 800 cc of an aqueous solution containing 100 g of silver nitrate and 860 cc of an aqueous solution containing 75 g of potassium bromide were added thereto over 60 minutes to prepare a silver iodobromide emulsion having a silver iodide content of 14 mol % and a mean grain size of 0.88 μm. The resulting emulsion was designated Emulsion 1. Emulsion 1 was found to comprise twins having an aspect ratio of 2.0 and a (111) facial ratio of 80%.

Emulsion 2 having a silver iodide content of 12 mol % was prepared by depositing an outer shell on 300 g of Emulsion b using silver nitrate totally amounting to 125 g in the same manner as for Emulsion 1. Similarly, Emulsions 3 to 5 were prepared from Emulsions c, d, and e, respectively.

Emulsions 6 to 9 were prepared in the same manner as for Emulsions 1 to 4, except for changing the conditions for shell deposition to a temperature of 60° C. and a pAg of 9.0 and using no compound of formula (18).

A mixture of 133 g of Emulsion b and 167 g of Emulsion d was subjected to shell deposition in the same manner as in the preparation of Emulsion 3 using 300 g of Emulsion c to prepare Emulsion 10.

A mixture of 50 g of Emulsion a, 50 g of Emulsion d, and 200 g of Emulsion c was subjected to shell deposition in the same manner as in the preparation of Emulsion 3 to prepare Emulsion 11.

Emulsions 12 and 13 were prepared in the same manner as for Emulsions 3 and 4, respectively, except for using no compound of formula (18).

Characteristic properties of the thus prepared emulsions are shown in Table 1 below.

TABLE 1

| Emulsion No. | AgI Content Core (mol %) | AgI Content Shell (mol %) | Core/Shell Ag Molar Ratio | Average AgI Content (mol %) | Distinct Stratiform Structure | Mean Grain Size (μm) | Coefficient of Variation of Grain Size | Aspect Ratio | Compound of Formula (A) |
|---|---|---|---|---|---|---|---|---|---|
| 1 | 42 | 0 | 1/2 | 14.0 | Yes | 0.88 | 0.20 | 2.0 | (18) |
| 2 | " | " | 1/2.5 | 12.0 | " | 0.86 | 0.19 | 1.9 | " |
| 3 | " | " | 1/3.2 | 10.0 | " | 0.86 | 0.19 | 1.9 | " |
| 4 | " | " | 1/4 | 8.4 | " | 0.88 | 0.18 | 1.8 | " |
| 5 | " | " | 1/6 | 6.0 | " | 0.87 | 0.18 | 1.6 | " |
| 6 | " | " | 1/2 | 14.0 | No | 0.89 | 0.21 | 2.2 | none |
| 7 | " | " | 1/2.5 | 12.0 | " | 0.87 | 0.20 | 2.0 | " |
| 8 | " | " | 1/3.2 | 10.0 | " | 0.86 | 0.20 | 2.0 | " |
| 9 | " | " | 1/4 | 8.4 | " | 0.87 | 0.19 | 1.9 | " |
| 10 | " | " | 1/3.2 | 10.0 | Yes | 0.87 | 0.22 | 2.0 | (18) |
| 11 | " | " | 1/3.2 | 10.0 | " | 0.87 | 0.27 | 2.2 | " |
| 12 | " | " | 1/3.2 | 10.0 | " | 0.87 | 0.20 | 1.9 | none |
| 13 | " | " | 1/4 | 8.4 | " | 0.87 | 0.20 | 1.9 | " |

Preparation of Light-Sensitive Material

The following layers were coated on a cellulose triacetate film support having a subbing layer to prepare a multi-layer color light-sensitive material. The resulting material was designated Sample 101.

| 1st Layer (Antihalation Layer): | |
|---|---|
| Black colloidal silver | 0.18 g-Ag/m$^2$ |
| Gelatin | 0.80 g/m$^2$ |
| 2nd Layer (Intermediate Layer): | |
| 2,5-Di-t-pentadecylhydro-quinone | 0.18 g/m$^2$ |
| EX-1 | 0.070 g/m$^2$ |
| EX-3 | 0.020 g/m$^2$ |
| EX-12 | 2.0 × 10$^{-3}$ g/m$^2$ |
| U-1 | 0.060 g/m$^2$ |
| U-2 | 0.080 g/m$^2$ |
| U-3 | 0.10 g/m$^2$ |
| HBS-1 | 0.10 g/m$^2$ |
| HBS-2 | 0.020 g/m$^2$ |
| Gelatin | 0.70 g/m$^2$ |
| 3rd Layer (1st Red-Sensitive Emulsion Layer): | |
| Emulsion A | 0.25 g-Ag/m$^2$ |
| Emulsion F | 0.25 g-Ag/m$^2$ |
| Sensitizing dye I | 6.9 × 10$^{-5}$ mol/mol-AgX (X: halogen) |
| Sensitizing dye II | 1.8 × 10$^{-5}$ mol/mol-AgX |
| Sensitizing dye III | 3.1 × 10$^{-4}$ mol/mol-AgX |
| EX-2 | 0.34 g/m$^2$ |
| EX-10 | 0.020 g/m$^2$ |
| U-1 | 0.070 g/m$^2$ |
| U-2 | 0.050 g/m$^2$ |
| U-3 | 0.070 g/m$^2$ |
| HBS-1 | 0.005 g/m$^2$ |
| Gelatin | 0.70 g/m$^2$ |
| 4th Layer (2nd Red-Sensitive Emulsion Layer): | |
| Emulsion G | 1.00 g-Ag/m$^2$ |
| Sensitizing dye I | 5.1 × 10$^{-5}$ mol/mol-AgX |
| Sensitizing dye II | 1.4 × 10$^{-5}$ mol/mol-AgX |
| Sensitizing dye III | 2.3 × 10$^{-4}$ mol/mol-AgX |
| EX-2 | 0.40 g/m$^2$ |
| EX-3 | 0.050 g/m$^2$ |
| EX-10 | 0.015 g/m$^2$ |
| U-1 | 0.070 g/m$^2$ |
| U-2 | 0.050 g/m$^2$ |
| U-3 | 0.070 g/m$^2$ |
| Gelatin | 0.95 g/m$^2$ |
| 5th Layer (3rd Red-Sensitive Emulsion Layer): | |

-continued

| | |
|---|---|
| Emulsion I | 1.60 g-Ag/m$^2$ |
| Sensitizing dye I | 5.4 × 10$^{-5}$ mol/mol-AgX |
| Sensitizing dye II | 1.4 × 10$^{-5}$ mol/mol-AgX |
| Sensitizing dye III | 2.4 × 10$^{-4}$ mol/mol-AgX |
| EX-2 | 0.097 g/m$^2$ |
| EX-3 | 0.010 g/m$^2$ |
| EX-4 | 0.080 g/m$^2$ |
| HBS-1 | 0.11 g/m$^2$ |
| HBS-2 | 0.05 g/m$^2$ |
| Gelatin | 1.20 g/m$^2$ |
| 6th Layer (Intermediate Layer): | |
| EX-5 | 0.040 g/m$^2$ |
| HBS-1 | 0.020 g/m$^2$ |
| Gelatin | 0.60 g/m$^2$ |
| 7th Layer (1st Green-Sensitive Emulsion Layer): | |
| Emulsion A | 0.15 g-Ag/m$^2$ |
| Emulsion F | 0.15 g-Ag/m$^2$ |
| Sensitizing dye IV | 3.0 × 10$^{-5}$ mol/mol-AgX |
| Sensitizing dye V | 1.0 × 10$^{-4}$ mol/mol-AgX |
| Sensitizing dye VI | 3.8 × 10$^{-4}$ mol/mol-AgX |
| EX-1 | 0.021 g/m$^2$ |
| Polymer coupler (P-13) | 0.26 g/m$^2$ |
| EX-7 | 0.030 g/m$^2$ |
| EX-8 | 0.025 g/m$^2$ |
| HBS-1 | 0.10 g/m$^2$ |
| HBS-3 | 0.010 g/m$^2$ |
| Gelatin | 0.63 g/m$^2$ |
| 8th Layer (2nd Green-Sensitive Emulsion Layer): | |
| Emulsion C | 0.45 g-Ag/m$^2$ |
| Sensitizing dye IV | 2.1 × 10$^{-5}$ mol/mol-AgX |
| Sensitizing dye V | 7.0 × 10$^{-5}$ mol/mol-AgX |
| Sensitizing dye VI | 2.6 × 10$^{-4}$ mol/mol-AgX |
| Polymer coupler (P-13) | 0.094 g/m$^2$ |
| EX-7 | 0.026 g/m$^2$ |
| EX-8 | 0.018 g/m$^2$ |
| HBS-1 | 0.16 g/m$^2$ |
| HBS-3 | 8.0 × 10$^{-3}$ g/m$^2$ |
| Gelatin | 0.50 g/m$^2$ |
| 9th Layer (3rd Green-Sensitive Emulsion Layer): | |
| Emulsion E | 0.10 g-Ag/m$^2$ |
| Sensitizing dye IV | 3.5 × 10$^{-5}$ mol/mol-Ag |
| Sensitizing dye V | 8.0 × 10$^{-5}$ mol/mol-Ag |
| Sensitizing dye VI | 3.0 × 10$^{-4}$ mol/mol-Ag |
| EX-1 | 0.025 g/m$^2$ |
| EX-11 | 0.10 g/m$^2$ |
| EX-13 | 0.010 g/m$^2$ |
| EX-6 | 0.025 g/m$^2$ |
| EX-8 | 0.010 g/m$^2$ |
| HBS-1 | 0.05 g/m$^2$ |
| HBS-2 | 0.05 g/m$^2$ |

| | -continued | |
|---|---|---|
| S-1 | 0.20 | g/m² |
| Gelatin | 0.80 | g/m² |

For improving preservability, processability, pressure resistance, antimicrobial and antifungal properties, antistatic properties, and coating properties, each of the 1st to 15th layers further contained W-1, W-2, W-3, B-4, B-5, F-1, F-2, F-3, F-4, F-5, F-6, F-7, F-8, F-9, F-10, F-11, F-12, F-13, and a salt of iron, lead, gold, platinum, iridium or rhodium.

Sample 101 thus obtained had a dry film thickness of 17.5 μm and a swollen film thickness of 24.0 μm.

Emulsions used in Sample 101 are shown in Table 2 below.

TABLE 2

| Emulsion No. | Average AgI Content (mol %) | Mean Grain Size (μm) | Coefficient of Variation of Grain Size (%) | Aspect Ratio | Grain Structure and Core/Shell Ag (or AgI) Molar Ratio | Distinct Stratiform Structure | Compound of Formula (A) |
|---|---|---|---|---|---|---|---|
| A | 4.0 | 0.45 | 27 | 1 | Double layer structure, 1/3 (13/1) | No | none |
| B | 4.0 | 0.55 | 14 | 1 | Double layer structure, 1/2 (12/0) | " | " |
| C | 4.0 | 0.60 | 30 | 2 | Double layer structure, 1/1 (8/0) | " | " |
| D | 4.0 | 0.90 | 35 | 2 | Double layer structure, 1/1 (8/0) | " | " |
| E | 4.0 | 0.90 | 35 | 3 | Double layer structure, 2/1 (6/0) | " | " |
| F | 4.0 | 0.25 | 28 | 1 | Double layer structure, 1/1 (8/0) | " | " |
| G | 4.0 | 0.60 | 25 | 2 | Double layer structure, 1/2 (12/0) | " | " |
| H | 4.0 | 1.05 | 25 | 3 | Double layer structure, 1/3 (16/0) | " | " |
| I | 1 | 0.07 | 15 | 1 | Uniform structure | " | " |

-continued

| 10th Layer (Yellow Filter Layer): | | |
|---|---|---|
| Gelatin | 1.05 | g/m² |
| Yellow colloidal silver | 0.050 | g-Ag/m² |
| EX-5 | 0.080 | g/m² |
| HBS-1 | 0.030 | g/m² |
| Gelatin | 0.75 | g/m² |
| 11th Layer (1st Blue-Sensitive Emulsion Layer): | | |
| Emulsion A | 0.080 | g-Ag/m² |
| Emulsion B | 0.070 | g-Ag/m² |
| Emulsion F | 0.070 | g-Ag/m² |
| Sensitizing dye VII | $3.5 \times 10^{-4}$ | mol/mol-AgX |
| EX-8 | 0.042 | g/m² |
| EX-9 | 0.72 | g/m² |
| HBS-1 | 0.28 | g/m² |
| Gelatin | 1.10 | g/m² |
| 12th Layer (2nd Blue-Sensitive Emulsion Layer): | | |
| Emulsion C | 0.45 | g-Ag/m² |
| Sensitizing dye VII | $2.1 \times 10^{-4}$ | mol/mol-AgX |
| EX-9 | 0.15 | g/m² |
| EX-10 | $7.0 \times 10^{-3}$ | g/m² |
| HBS-1 | 0.050 | g/m² |
| Gelatin | 0.60 | g/m² |
| 13th Layer (3rd Blue-Sensitive Emulsion Layer): | | |
| Emulsion H | 0.77 | g-Ag/m² |
| Sensitizing dye VII | $2.2 \times 10^{-4}$ | mol/mol-AgX |
| EX-9 | 0.20 | g/m² |
| HBS-1 | 0.070 | g/m² |
| Gelatin | 0.69 | g/m² |
| 14th Layer (1st Protective Layer): | | |
| Emulsion I | 0.20 | g-Ag/m² |
| U-4 | 0.11 | g/m² |
| U-5 | 0.17 | g/m² |
| HBS-1 | $5.0 \times 10^{-2}$ | g/m² |
| Gelatin | 0.70 | g/m² |
| 15th Layer (2nd Protective Layer): | | |
| H-1 | 0.30 | g/m² |
| B-1 (diameter: 1.7 μm) | $5.0 \times 10^{-2}$ | g/m² |
| B-2 (diameter: 1.7 μm) | 0.10 | g/m² |
| B-3 | 0.10 | g/m² |

Additives used in Sample 101 are shown below.

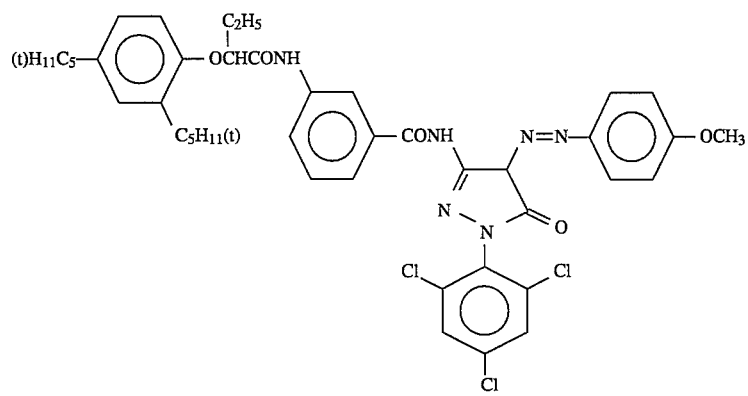
EX-1
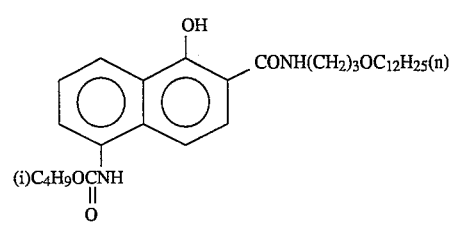
EX-2
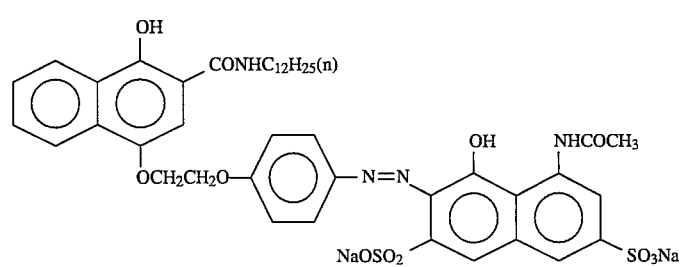
EX-3
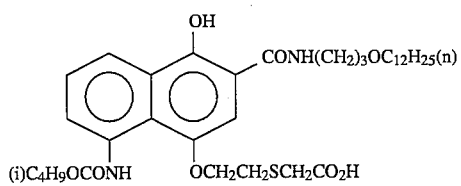
EX-4
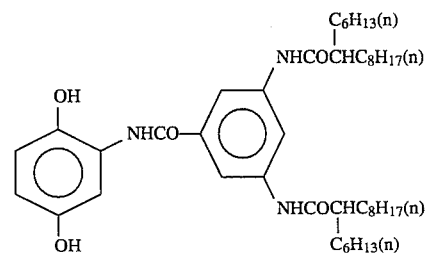
EX-5
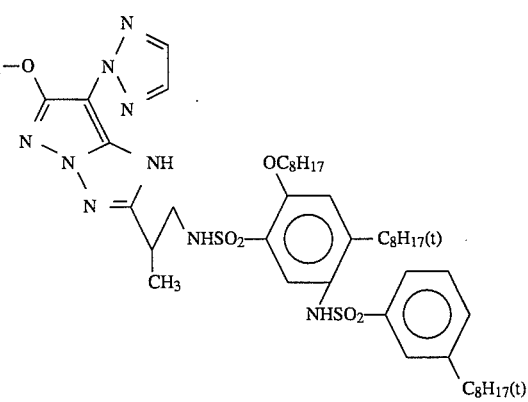
EX-6

EX-7
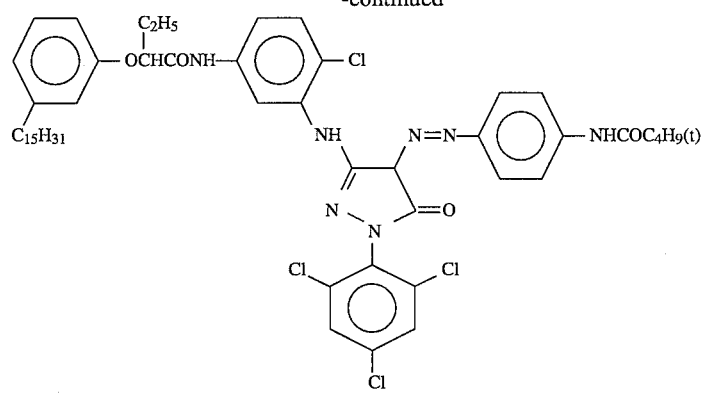
(49) of JP-A-57-151944, (D-14) of JP-A-1-269935 and (D-14) of JP-A-2-28637
EX-8
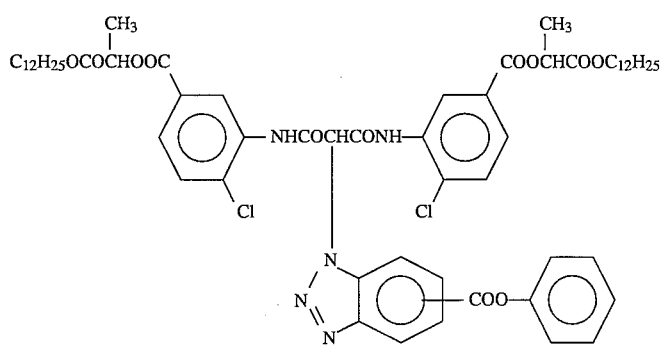
EX-9
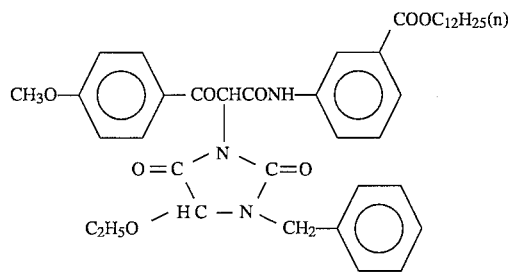
EX-10

-continued
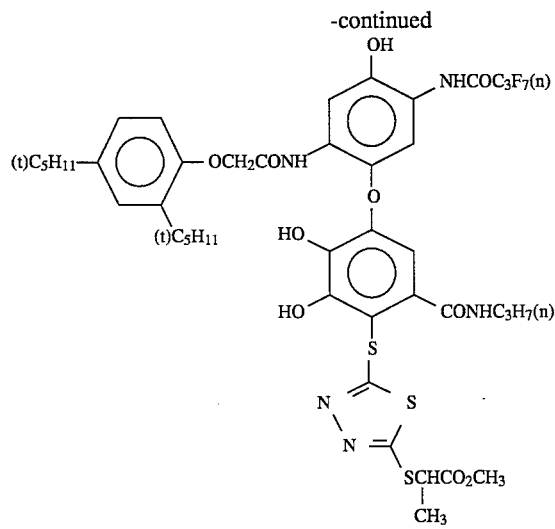
EX-11
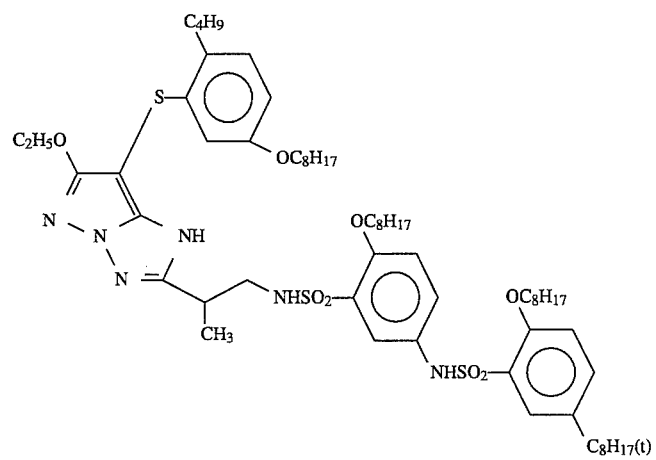
EX-12
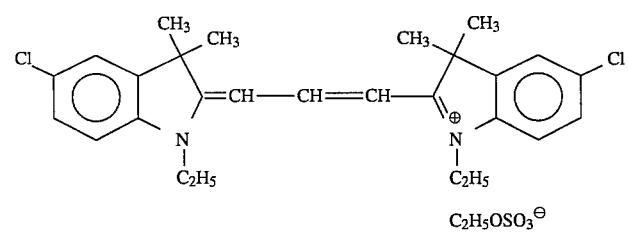
EX-13

-continued
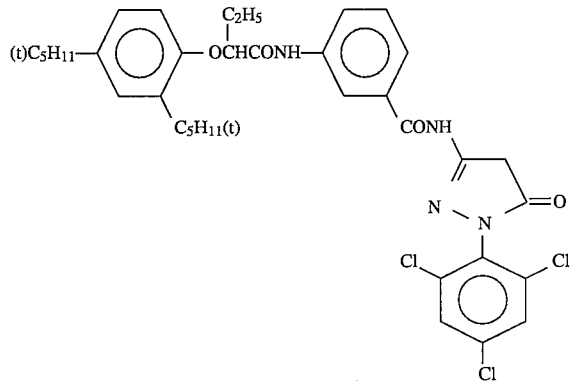
EX-14 ((D-12) of JP-A-1-259359)
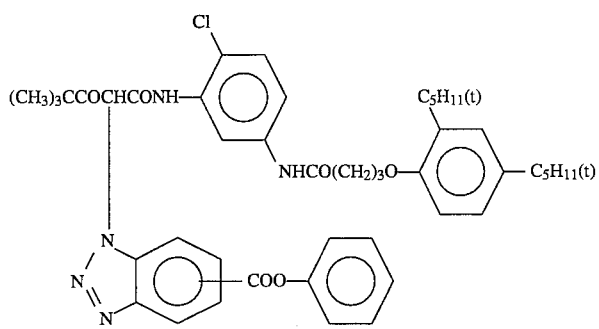
EX-15 (Compound 27 of U.S. Pat. No. 4,782,012)
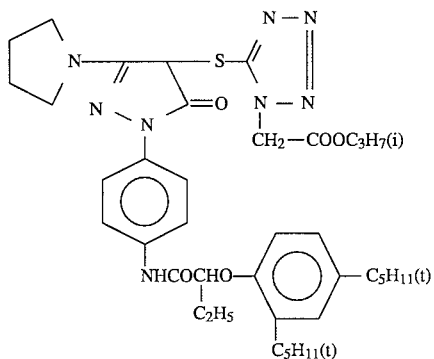
U-1
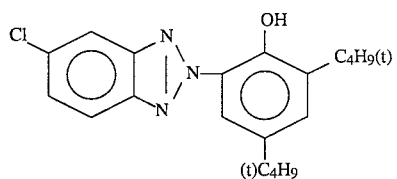
U-2
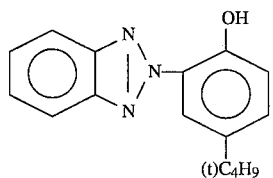
U-3

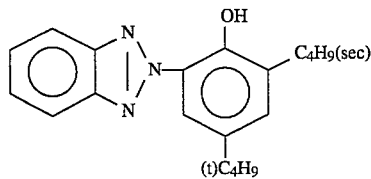
U-4
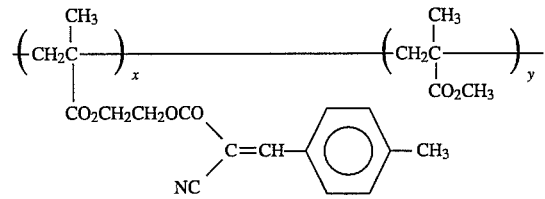
x:y = 70:30 (wt %)
U-5
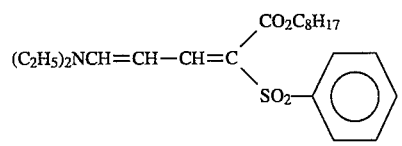
HBS-1
Tricresyl phosphate
HBS-2
Di-n-butyl phthalate
HBS-3
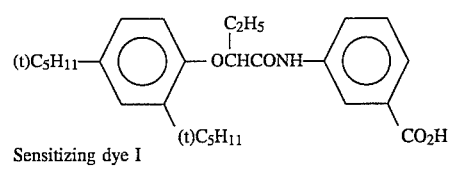
Sensitizing dye I
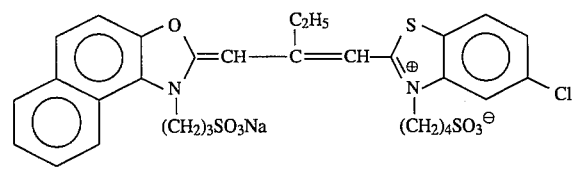
Sensitizing dye II
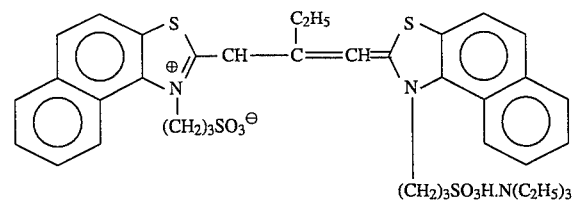
Sensitizing dye III -continued
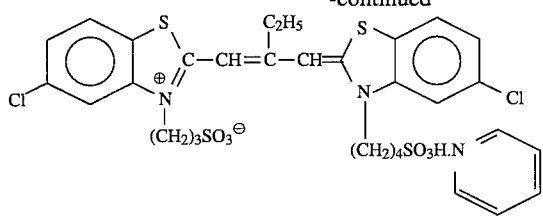
Sensitizing dye IV
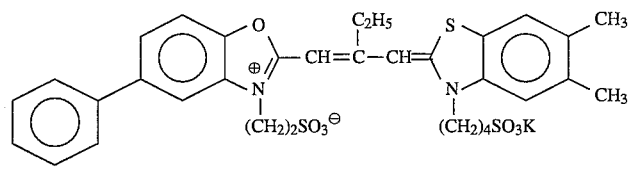
Sensitizing dye V
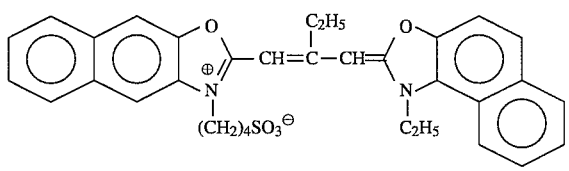
Sensitizing dye VI
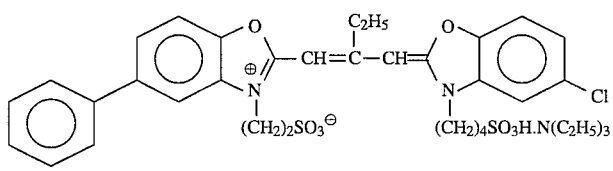
Sensitizing dye VII
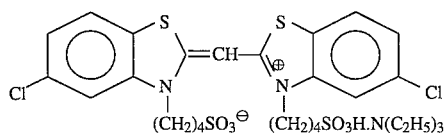
S-1
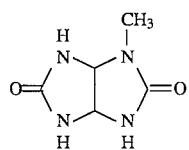
H-1
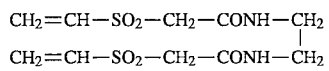
B-1
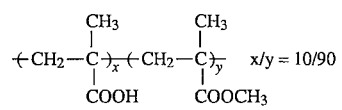   x/y = 10/90
B-2

-continued
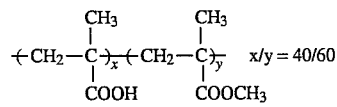
B-3
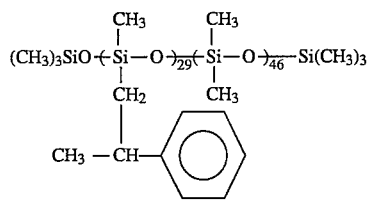
B-4
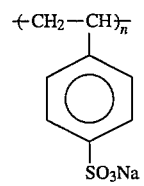
B-5
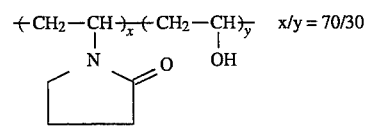
W-1
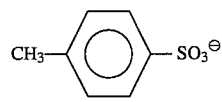
W-2
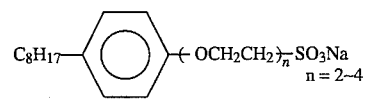
W-3
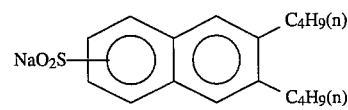
F-1
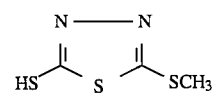
F-2

-continued
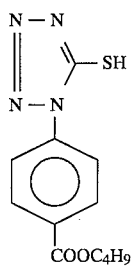
F-3
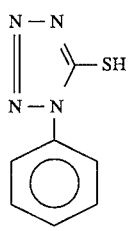
F-4
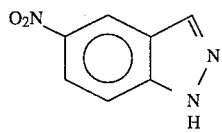
F-5
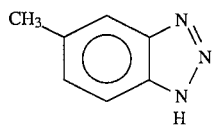
F-6
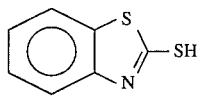
F-7
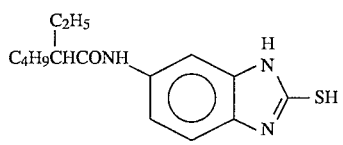
F-8
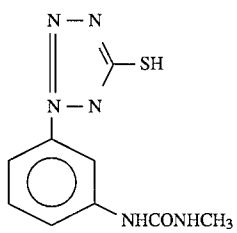
F-9
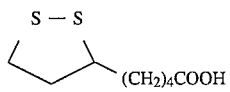

-continued

F-10

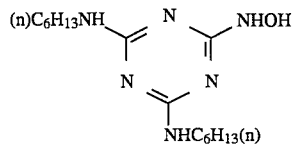

F-11

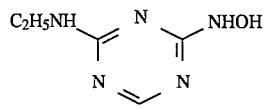

F-12

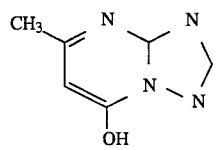

F-13

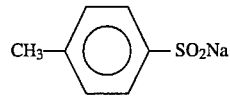

Samples 102 to 114 were prepared in the same manner as for Sample 101, except for replacing Emulsion I used in the 5th layer of Sample 101 with the emulsion shown in Table 3 below.

Samples 115 to 128 were prepared in the same manner as for Samples 101, respectively, except for replacing the DIR coupler (EX-8) used in the 7th, 8th and 9th layers with an equimolar amount a DIR coupler (D-5) according to the present invention.

Sample 129 was prepared in the same manner as for Sample 117, except for replacing the coupler (P-13) used in the 7th and 8th layers of Sample 117 with 1.25 times the weight of a coupler (P-14), increasing the amount of HBS-1 in the same layers to 1.2 times, and increasing the amount of gelatin in the same layers to 1.2 times.

Sample 130 was prepared in the same manner as for Sample 117, except for replacing the coupler (P-13) used in the 7th and 8th layers of Sample 117 with 1.5 times the weight of (EX-13), doubling the amount of HBS-1 in the same layers, and increasing the amount of gelatin in the same layers to 1.4 times.

Processing and Evaluations

Relative sensitivity of the green-sensitive layer of Sample 129 and 130 was the same as that of Sample 117 when processed according to the color development processing hereinafter described. Further, these samples showed substantially no difference in scratch resistance when tested with a sapphire stylus having a diameter of 0.05 mm and were confirmed to be substantially equal in both film strength and photographic performance.

After imagewise exposed to green light, each sample was uniformly exposed to red light at such an exposure amount that the green light-unexposed area of Sample 101 might have a cyan density of 0.8 when processed as follows and then subjected to development processing.

Further, each sample was imagewise exposed to white light, and a relative sensitivity was determined from a logarithm of a reciprocal of an exposure amount which provided a cyan density of fog+0.4.

Furthermore, granularity of the sample was evaluated by obtaining an RMS value at a cyan density of fog+0.4 in a usual manner.

In addition, sharpness of the sample was evaluated by obtaining an MTF value in a usual manner.

The results of these evaluations are shown in Table 3.

Development processing for the evaluations was carried out at 38° C. according to the following conditions.

| 1. Color development | 3'15" |
|---|---|
| 2. Bleach | 6'30" |
| 3. Washing | 3'15" |
| 4. Fixing | 6'30" |
| 5. Washing | 3'15" |
| 6. Stabilization | 3'15" |

Processing solutions used in these steps had the following formulations.

Color Developing Solution Formulation:

| Sodium nitrilotriacetate | 1.0 g |
|---|---|
| Sodium sulfite | 4.0 g |
| Sodium carbonate | 30.0 g |
| Potassium bromide | 1.3 g |
| Hydroxylamine sulfate | 2.4 g |
| 4-(N-Ethyl-N-β-hydroxyethylamino)-2-methylaniline sulfate | 4.5 g |
| Water to make | 1 l |

Bleaching Solution Formulation:

-continued

| | |
|---|---|
| Ammonium bromide | 160.0 g |
| Aqueous ammonia (28%) | 25.0 ml |
| Sodium (ethylenediaminetetraacetato) iron | 130 g |
| Glacial acetic acid | 14 ml |
| Water to make | 1 l |
| Fixing Solution Formulation: | |
| Sodium tetrapolyphosphate | 2.0 g |
| Sodium sulfite | 4.0 g |
| Ammonium thiosulfate (70%) | 175.0 ml |
| Sodium bisulfite | 4.6 g |
| Water to make | 1 l |
| Stabilizing Solution Formulation: | |
| Formalin | 2.0 ml |
| Water to make | 1 l |

The above-prepared film roll of 36 exposures was continuously developed using the same processing solutions while replenishing with the respective replenisher described below for 10 days at a rate of 40 rolls per day. After the continuous processing, each of the samples separately imagewise exposed to white light was automatically developed in the same manner as described above, and sensitivity and gamma of the magenta image were measured.

The results obtained are shown in Table 4.

The color development processing was carried out as follows in an automatic developing machine at 38° C.

| | |
|---|---|
| 1. Development: | 3'15" |
| 2. Bleach | 1' |
| 3. Blix | 3'15" |

TABLE 3

| Sample No. | Emulsion in 5th Layer | DIR Coupler in 7th, 8th, and 9th Layers | Relative Sensitivity | RMS Value (×1000) | Degree of Color Turbidity | Cyan Image MTF Value (25 c/mm) | Remark |
|---|---|---|---|---|---|---|---|
| 101 | 1 | EX-8 | 0.00 | 2.45 | +0.03 | 55 | Comparison |
| 102 | 2 | " | 0.00 | 24.6 | +0.03 | 55 | " |
| 103 | 3 | " | 0.01 | 24.8 | +0.03 | 55 | " |
| 104 | 4 | " | 0.01 | 24.9 | +0.03 | 55 | " |
| 105 | 5 | " | 0.01 | 25.0 | +0.02 | 55 | " |
| 106 | 6 | " | −0.06 | 26.8 | +0.05 | 53 | " |
| 107 | 7 | " | −0.05 | 26.8 | +0.05 | 54 | " |
| 108 | 8 | " | −0.04 | 26.6 | +0.05 | 54 | " |
| 109 | 9 | " | −0.04 | 26.5 | +0.04 | 54 | " |
| 110 | 10 | " | 0.00 | 25.5 | +0.03 | 55 | " |
| 111 | 11 | " | 0.00 | 26.1 | +0.04 | 54 | " |
| 112 | 12 | " | −0.02 | 25.3 | +0.03 | 55 | " |
| 113 | 13 | " | −0.02 | 25.5 | +0.03 | 55 | " |
| 114 | D | " | −0.01 | 26.6 | +0.04 | 54 | " |
| 115 | 1 | D-5 | 0.00 | 24.0 | −0.01 | 58 | Invention |
| 116 | 2 | D-5 | 0.01 | 24.1 | −0.01 | 58 | Invention |
| 117 | 3 | " | 0.01 | 24.3 | −0.01 | 58 | " |
| 118 | 4 | " | 0.01 | 24.5 | −0.01 | 58 | " |
| 119 | 5 | " | 0.01 | 24.6 | −0.01 | 58 | " |
| 120 | 6 | " | −0.06 | 26.4 | +0.01 | 56 | Comparison |
| 121 | 7 | " | −0.05 | 26.3 | +0.01 | 56 | " |
| 122 | 8 | " | −0.04 | 26.1 | +0.01 | 56 | " |
| 123 | 9 | " | 0.04 | 25.1 | +0.01 | 57 | " |
| 124 | 10 | " | 0.01 | 25.2 | 0.01 | 58 | Invention |
| 125 | 11 | " | 0.00 | 25.6 | +0.01 | 58 | " |
| 126 | 12 | " | 0.00 | 24.9 | 0.00 | 58 | " |
| 127 | 13 | " | 0.00 | 25.1 | 0.00 | 58 | " |
| 128 | D | " | −0.01 | 26.1 | +0.01 | 57 | Comparison |
| 129 | 3 | " | 0.01 | 24.3 | 0.00 | 56 | Invention |
| 130 | 3 | " | 0.00 | 2.42 | +0.01 | 54 | " |

As can be seen from the results in Table 3, only those samples using the specific emulsion and DIR couplers according to the present invention exhibit high sensitivity, excellent graininess in terms of RMS value, excellent sharpness in terms of MTF value, and excellent color reproducibility in terms of color contamination.

Each of Samples 101 to 105, 115 to 119, 126, and 127 was cut to 35 mm wide strip, fabricated into a J 135 film of 36 exposures and loaded in a patrone. Thirty-six shots of a gray chart having a reflectance of 18% were taken on the film under the condition of ISO 400.

Each of the samples separately imagewise exposed to white light was automatically developed with processing solutions shown below, and sensitivity and gamma of the magenta image were measured.

-continued

| | |
|---|---|
| 4. Washing (1) | 40" |
| 5. Washing (2) | 1' |
| 6. Stabilization | 40" |
| 7. Drying (50° C.) | 1'15" |

Washing was conducted in a counter-flow system of from tank (2) toward tank (1).

The processing solutions had the following formulations. The rate of replenishment was 1200 ml/m$^2$ for color development, and 800 ml/m$^2$ for other processing steps inclusive of washing. The amount of a prebath carried over into the washing step was 50 ml/m$^2$.

Color Developing Solution Formulation

|  | Running Solution | Replenisher |
|---|---|---|
| Diethylenetriaminepentaacetic acid | 1.0 g | 1.1 g |
| 1-Hydroxyethylidene-1,1-diphosphonic acid | 2.0 g | 2.2 g |
| Sodium sulfite | 4.0 g | 4.4 g |
| Potassium carbonate | 30.0 g | 30.0 g |
| Potassium bromide | 1.4 g | 0.7 g |
| Potassium iodide | 1.3 mg | — |
| Hydroxylamine sulfate | 2.4 g | 2.6 g |
| 4-(N-Ethyl-N-β-hydroxyethyl-amino)-2-methylaniline sulfate | 4.5 g | 5.0 g |
| Water to make | 1.0 l | 1.0 l |
| pH | 10.0 | 10.05 |

Bleaching Solution Formulation

Both the running solution and the replenisher had the same composition.

| | |
|---|---|
| Ammonium (ethylenediamine-tetraacetato)iron (II) | 120.0 g |
| Disodium ethylenediamine-tetraacetate | 10.0 g |
| Ammonium nitrate | 10.0 g |
| Ammonium bromide | 100.0 g |
| Bleaching accelerator: | $5 \times 10^{-3}$ mol |

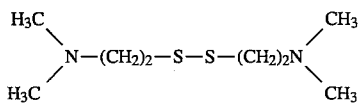

| | |
|---|---|
| Aqueous ammonia to adjust to | pH 6.3 |
| Water to make | 1.0 l |

Blix Solution Formulation

The running solution and the replenisher had the same composition.

| | |
|---|---|
| Ammonium (ethylenediamine-tetraacetato)iron (II) | 50.0 g |
| Disodium ethylenediamine-tetraacetate | 5.0 g |
| Sodium sulfite | 12.0 g |
| Ammonium thiosulfate aqueous solution (70%) | 240 ml |
| Aqueous ammonia to adjust to | pH 7.3 |
| Water to make | 1 l |

Washing Water

Tap water containing 32 mg/l of a calcium ion and 7.3 mg/l of a magnesium ion was passed through a column packed with an H-type strongly acidic cation exchange resin and an OH-type strongly basic anion exchange resin to reduce the calcium ion to 1.2 mg/l and the magnesium ion to 0.4 mg/l, and to the thus treated water was added 20 mg/l of sodium dichloroisocyanurate.

Stabilizing Solution Formulation

The running water and the replenisher had the same composition.

| | |
|---|---|
| Formalin (37 w/v %) | 2.0 ml |
| Polyoxyethylene-p-monononylphenyl ether (degree of polymerization: 10) | 0.3 g |
| Disodium ethylenediaminetetraacetate | 0.005 g |
| Water to make | 1 l |
| pH | 5.8 |

Drying temperature was 50° C.

TABLE 4

| | | Before Continuous Processing | | After Continuous Processing | | | |
|---|---|---|---|---|---|---|---|
| Sample No. | Emulsion | DIR Coupler | Compound of Formula (A) | Sensitivity* | Gamma** | Sensitivity* | Gamma** | Remark |
| 101 | 1 | EX-8 | (18) | 0.00 | 0.69 | 0.30 | 0.74 | Comparison |
| 102 | 2 | " | " | 0.00 | 0.69 | 0.03 | 0.74 | " |
| 103 | 3 | " | " | 0.01 | 0.69 | 0.03 | 0.74 | " |
| 104 | 4 | " | " | 0.01 | 0.70 | 0.04 | 0.74 | " |
| 105 | 5 | " | " | 0.01 | 0.70 | 0.05 | 0.75 | " |
| 115 | 1 | D-5 | " | 0.00 | 0.69 | 0.00 | 0.69 | Invention |
| 116 | 2 | " | " | 0.01 | 0.70 | 0.01 | 0.70 | " |
| 117 | 3 | " | " | 0.01 | 0.70 | 0.01 | 0.70 | " |
| 118 | 4 | " | " | 0.01 | 0.71 | 0.02 | 0.72 | " |
| 119 | 5 | " | " | 0.01 | 0.71 | 0.02 | 0.72 | " |
| 129 | 12 | " | — | 0.00 | 0.68 | 0.02 | 0.70 | " |
| 130 | 13 | " | — | 0.00 | 0.68 | 0.02 | 0.71 | " |

Note:
*Relative value of a logarithm of a reciprocal of an exposure amount which provided a magenta density of (fog + 0.2).
**A slope of a straight line connecting a density point of (fog + 0.2) and a density point of (fog + 1.0).

It can be seen from Table 4 that the light-sensitive materials according to the present invention are not liable to variation in photographic performance even when processed in a continuous manner while supplying a developing solution for replenishment.

EXAMPLE 2

Samples 201 to 210 were prepared in the same manner as for Sample 116, except for replacing (D-5) in the 7th, 8th, and 9th layers of Sample 116 with the DIR coupler shown in Table 5 below. The amount of the DIR coupler was selected so as to give substantially the same sensitivity and gamma as in Sample 116.

The resulting samples were evaluated in the same manner as in Example 1, and the results obtained are shown in Table 5.

TABLE 5

| | DIR Coupler | | | | Before Continuous Processing | | After Continuous Processing | | |
|---|---|---|---|---|---|---|---|---|---|
| Sample No. | Kind | Amount (mol) | MTF Value | Degree of Turbidity | Color tivity | Sensi-Gamma | Sensi-tivity | Gamma | Remark |
| 116 | D-5 | 1.0 | 58 | −0.01 | 0.01 | 0.70 | 0.01 | 0.70 | Invention |
| 201 | D-1 | 1.0 | 58 | −0.02 | 0.01 | 0.69 | 0.01 | 0.69 | " |
| 202 | D-7 | 0.8 | 58 | −0.02 | 0.00 | 0.69 | 0.01 | 0.69 | " |
| 203 | D-8 | 0.8 | 58 | −0.02 | 0.01 | 0.69 | 0.01 | 0.69 | " |
| 204 | D-9 | 0.8 | 57 | −0.01 | 0.00 | 0.69 | 0.01 | 0.69 | " |
| 205 | D-20 | 1.8 | 57 | −0.01 | 0.02 | 0.71 | 0.02 | 0.71 | " |
| 206 | EX-14 | 3.0 | 56 | +0.02 | 0.02 | 0.69 | 0.04 | 0.74 | Comparison |
| 207 | EX-15 | 4.0 | 54 | +0.04 | 0.02 | 0.69 | 0.03 | 0.72 | " |
| 208 | EX-16 | 3.5 | 56 | −0.01 | 0.01 | 0.70 | −0.02 | 0.67 | " |
| 209* | EX-17 | 4.0 | 52 | +0.07 | 0.06 | 0.79 | 0.06 | 0.79 | " |
| 210** | EX-18 | 4.0 | 55 | +0.01 | 0.01 | 0.70 | 0.03 | 0.74 | " |

NOte:
*:Sample 209 did not provide a development inhibition as is shown in Table 5. This means EX-17 did not function as a DIR coupler. It seems the formula of EX-17 shown in EP-A-233,641 is incorrect.
**:EX-17 itself did not provide a DIR activity as is seen in Sample 209. The formula of EX-17 seems to be incorrect. Therefore, in Sample 210, EX-18 which would be an intended DIR coupler was used.
EX-16(U.S. Pat. No. 5,126,236, Compound (131))

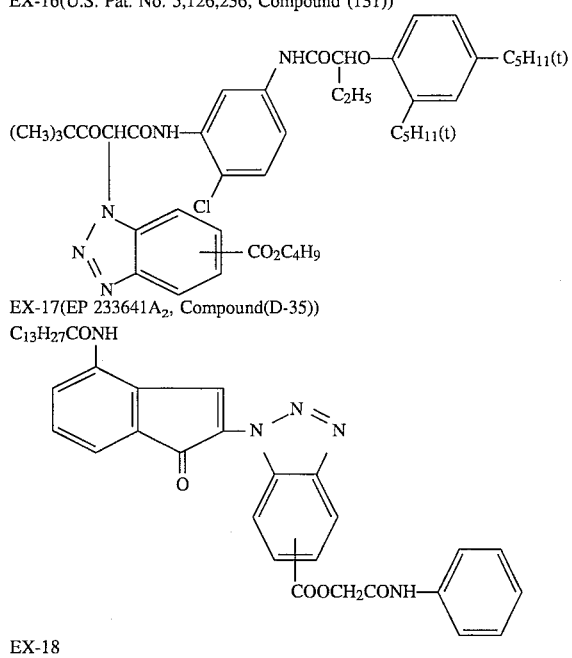

EX-17(EP 233641A$_2$, Compound(D-35))

EX-18

TABLE 5-continued

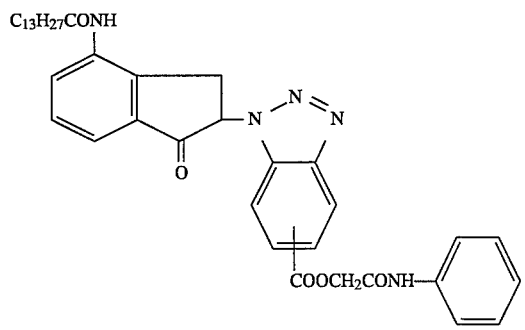

It can be seen from Table 5 that the samples according to the present invention undergo less variations in photographic performance even when continuously processed while exhibiting excellent image sharpness and color reproducibility.

EXAMPLE 3

A light-sensitive material was prepared in the same manner as for Sample 212 of JP-A-1-269935, except for replacing (EX-8) and (EX-10) with an equimolar amount of DIR couplers (D-5) and (D-27) of the present invention, respectively. The resulting sample was evaluated in the same manner as in Example 1. As a result, the sample underwent only small variations in photographic performance even when continuously processed while exhibiting excellent color reproducibility and sharpness.

While the invention has been described in detail and with reference to specific examples thereof, it will be apparent to one skilled in the art that various changes and modifications can be made therein without departing from the spirit and scope thereof.

What is claimed is:

1. A silver halide color photographic material comprising a support having thereon at least one light-sensitive silver halide emulsion layer, wherein said light-sensitive material contains a DIR coupler represented by formula (I):

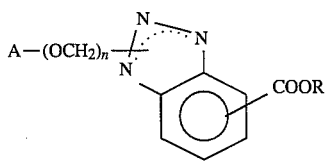

wherein A represents a coupler residue; R represents an alkyl group having from 1 to 4 carbon atoms substituted with at least one of an alkoxy carbonyl group or an alkylcarbamoyl group; and n represents 1 when A represents a phenol type or naphthol type coupler residue, or n represents 0 when A represents other coupler residues, and said emulsion layer contains chemically sensitized silver halide grains which individually have a distinct stratiform structure comprising silver iodobromide containing from 7 to 45 mol % of silver iodide and which individually have an overall silver iodide content of more than 4 mol %.

2. The silver halide color photographic material as claimed in claim 1, wherein said photographic material further contains a compound represented by formula (A):

$$Q-SM^1 \qquad (A)$$

wherein Q represents a heterocyclic ring residue having directly or indirectly bonded thereto at least one group selected from the group consisting of $-SO_3M^2$, $-COOM^2$, $-OH$, and $-NR^1R^2$; $M^1$ and $M^2$ each represent a hydrogen atom, an alkali metal, a quaternary ammonium group, or a quaternary phosphonium group; and $R^1$ and $R^2$ each represent a hydrogen atom or a substituted or unsubstituted alkyl group.

3. The silver halide color photographic material as claimed in claim 1, wherein said silver halide grains have a coefficient of variation of not more than 0.25 with respect to their grain size.

4. The silver halide color photographic material as claimed in claim 2, wherein said silver halide grains have a coefficient of variation of not more than 0.25 with respect to their grain size.

5. The silver halide color photographic material as claimed in claim 1, wherein said photographic material has at least one red-sensitive silver halide emulsion layer containing a cyan coupler, at least one green-sensitive silver halide emulsion layer containing a magenta coupler, and at least one blue-sensitive silver halide emulsion layer containing a yellow coupler, skid green-sensitive silver halide emulsion layer containing a magenta polymer coupler.

6. The silver halide color photographic material as claimed in claim 2, wherein said photographic material has at least one red-sensitive silver halide emulsion layer containing a cyan coupler, at least one green-sensitive silver halide emulsion layer containing a magenta coupler, and at least one blue-sensitive silver halide emulsion layer containing a yellow coupler, said green-sensitive silver halide emulsion layer containing a magenta polymer coupler.

7. The silver halide color photographic material as claimed in claim 3, wherein said photographic material has at least one red-sensitive silver halide emulsion layer containing a cyan coupler, at least one green-sensitive silver halide emulsion layer containing a magenta coupler, and at least one blue-sensitive silver halide emulsion layer containing a yellow coupler, said green-sensitive silver halide emulsion layer containing a magenta polymer coupler.

8. The silver halide color photographic material as claimed in claim 4, wherein said photographic material has at least one red-sensitive silver halide emulsion layer containing a cyan coupler, at least one green-sensitive silver halide emulsion layer containing a magenta coupler, and at least one blue-sensitive silver halide emulsion layer containing a yellow coupler, said green-sensitive silver halide emulsion layer containing a magenta polymer coupler.

9. The silver halide color photographic material as claimed in claim 5, wherein said magenta coupler is a polymer coupler comprising a monomer represented by formula (PA):

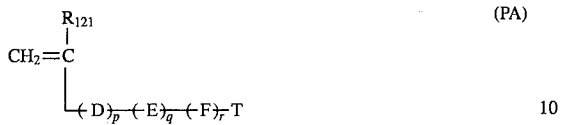

wherein $R_{121}$ represents a hydrogen atom, an alkyl group having from 1 to 4 carbon atoms, or a chlorine atom; —D— represents —COO—, —CONR$_{122}$—, or a substituted or unsubstituted phenyl group; —E— represents a substituted or unsubstituted alkylene group, a substituted or unsubstituted phenylene group, or a substituted or unsubstituted aralkylene group; —F— represents —CONR$_{122}$—, —NR$_{122}$CONR$_{122}$—, —NR$_{122}$COO—, —NR$_{122}$CO—, —OCONR$_{122}$—, —NR$_{122}$—, —COO—, —OCO—, —CO—, —O—, —S—, —SO$_2$—, —NR$_{122}$SO$_2$—, or —SO$_2$NR$_{122}$—; $R_{122}$ represents a hydrogen atom, a substituted or unsubstituted aliphatic group, or a substituted or unsubstituted aryl group; plural $R_{122}$ groups, if any in the same molecule, may be the same or different; p, q, and r each represent 0 or 1, provided that they do not simultaneously represent 0; and T represents a magenta coupler residue represented by formula (PB) shown below which is bonded to the moiety at any of the Ar, Z, and $R_{133}$ moieties described below.

wherein Ar represents a group known as a substituent at the 1-position of 2-pyrazolin-5-one couplers; $R_{133}$ represents a substituted or unsubstituted anilino group, a substituted or unsubstituted acylamino group, a substituted or unsubstituted ureido group, or a substituted or unsubstituted sulfonamido group; and Z represents a hydrogen atom, a halogen atom, or a coupling releasable group bonded via an oxygen atom, a nitrogen atom, or a sulfur atom.

10. The silver halide color photographic material as claimed in claim 6, wherein said magenta coupler is a polymer coupler comprising a monomer represented by formula (PA):

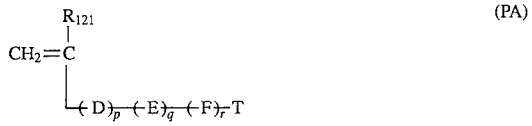

wherein $R_{121}$ represents a hydrogen atom, an alkyl group having from 1 to 4 carbon atoms, or a chlorine atom; —D— represents —COO—, —CONR$_{122}$—, or a substituted or unsubstituted phenyl group; —E— represents a substituted or unsubstituted alkylene group, a substituted or unsubstituted phenylene group, or a substituted or unsubstituted aralkylene group; —F— represents —CONR$_{122}$—, —NR$_{122}$CONR$_{122}$—, —NR$_{122}$COO—, —NR$_{122}$CO—, —OCONR$_{122}$—, —NR$_{122}$—, —COO—, —OCO—, —CO—, —O—, —S—, —SO$_2$—, —NR$_{122}$SO$_2$—, or —SO$_2$NR$_{122}$—; $R_{122}$ represents a hydrogen atom, a substituted or unsubstituted aliphatic group, or a substituted or unsubstituted aryl group; plural $R_{122}$ groups, if any in the same molecule, may be the same or different; p, q, and r each represent 0 or 1, provided that they do not simultaneously represent 0; and T represents a magenta coupler residue represented by formula (PB) shown below which is bonded to the moiety at any of the Ar, Z, and $R_{133}$ moieties described below,

wherein Ar represents a group known as a substituent at the 1-position of 2-pyrazolin-5-one couplers; $R_{133}$ represents a substituted or unsubstituted anilino group, a substituted or unsubstituted acylamino group, a substituted or unsubstituted ureido group, or a substituted or unsubstituted sulfonamido group; and Z represents a hydrogen atom, a halogen atom, or a coupling releasable group bonded via an oxygen atom, a nitrogen atom, or a sulfur atom.

11. The silver halide color photographic material as claimed in claim 7, wherein said magenta coupler is a polymer coupler comprising a monomer represented by formula (PA):

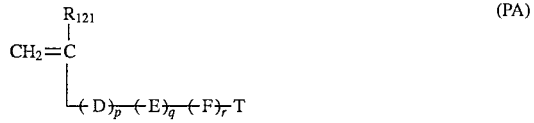

wherein $R_{121}$ represents a hydrogen atom, an alkyl group having from 1 to 4 carbon atoms, or a chlorine atom; —D— represents —COO—, —CONR$_{122}$—, or a substituted or unsubstituted phenyl group; —E— represents a substituted or unsubstituted alkylene group, a substituted or unsubstituted phenylene group, or a substituted or unsubstituted aralkylene group; —F— represents —CONR$_{122}$—, —NR$_{122}$CONR$_{122}$—, —NR$_{122}$COO—, —NR$_{122}$CO—, —OCONR$_{122}$—, —NR$_{122}$—, —COO—, —OCO—, —CO—, —O—, —S—, —SO$_2$—, —NR$_{122}$SO$_2$—, or —SO$_2$NR$_{122}$—; $R_{122}$ represents a hydrogen atom, a substituted or unsubstituted aliphatic group, or a substituted or unsubstituted aryl group; plural $R_{122}$ groups, if any in the same molecule, may be the same or different; p, q, and r each represent 0 or 1, provided that they do not simultaneously represent 0; and T represents a magenta coupler residue represented by formula (PB) shown below which is bonded to the moiety at any of the Ar, Z, and $R_{133}$ moieties described below,

wherein Ar represents a group known as a substituent at the 1-position of 2-pyrazolin-5-one couplers; $R_{133}$ represents a substituted or unsubstituted anilino group, a substituted or unsubstituted acylamino group, a substituted or unsubstituted ureido group, or a substituted or unsubstituted sulfonamido group; and Z represents a hydrogen atom, a halogen 12. The silver halide color photographic material as claimed in claim 8, wherein said magenta coupler is a polymer coupler comprising a monomer represented by formula (PA):

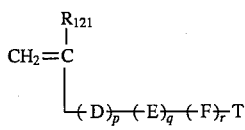     (PA)

wherein $R_{121}$ represents a hydrogen atom, an alkyl group having from 1 to 4 carbon atoms, or a chlorine atom; —D— represents —COO—, —CONR$_{122}$—, or a substituted or unsubstituted phenyl group; —E— represents a substituted or unsubstituted alkylene group, a substituted or unsubstituted phenylene group, or a substituted or unsubstituted aralkylene group; —F— represents —CONR$_{122}$—, —NR$_{122}$CONR$_{122}$—, —NR$_{122}$COO—, —NR$_{122}$CO—, —OCONR$_{122}$—, —NR$_{122}$—, —COO—, —OCO—, —CO—, —O—, —S—, —SO$_2$—, —NR$_{122}$SO$_2$—, or —SO$_2$NR$_{122}$—; $R_{122}$ represents a hydrogen atom, a substituted or unsubstituted aliphatic group, or a substituted or unsubstituted aryl group; plural $R_{122}$ groups, if any in the same molecule, may be the same or different; p, q, and r each represent 0 or 1, provided that they do not simultaneously represent 0; and T represents a magenta coupler residue represented by formula (PB) shown below which is bonded to the moiety at any of the At, Z, and $R_{133}$ moieties described below:

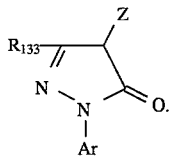     (PB)

13. The silver halide color photographic material as claimed in claim 1, wherein A is a yellow coupler residue, a magenta coupler residue, a cyan coupler residue or a colorless coupler residue.

14. The silver halide color photographic material as claimed in claim 1, wherein A is selected from the group consisting of formulae (Cp-1), (Cp-2), (Cp-3), (Cp-4), (Cp-5), (Cp-6), (Cp-7), (Cp-8), (Cp-9) and (Cp-10)

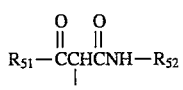     (Cp-1)

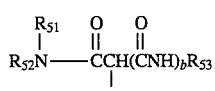     (Cp-2)

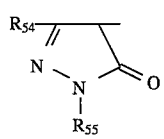     (Cp-3)

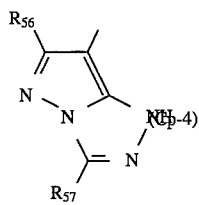     (Cp-4)

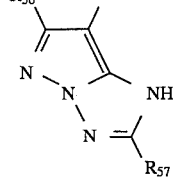     (Cp-5)

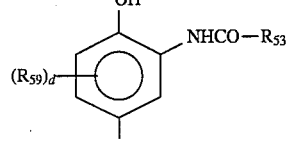     (Cp-6)

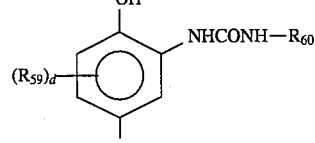     (Cp-7)

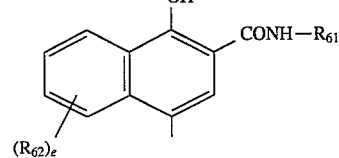     (Cp-8)

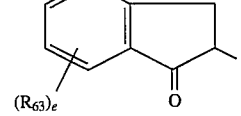     (Cp-9)

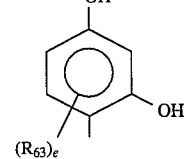     (Cp-10)

wherein in formulae (Cp-1) through (Cp-10), each free bond indicates a coupling position at which a coupling releasable group is bonded; when $R_{51}$, $R_{52}$, $R_{53}$, $R_{54}$, $R_{55}$, $R_{56}$, $R_{57}$, $R_{59}$, $R_{60}$, $R_{61}$, $R_{62}$, or $R_{63}$ contains an antidiffusion group, each of said $R_{51}$–$R_{57}$ and $R_{59}$–$R_{63}$ is selected so as to have a total carbon atom number of from 8 to 40, otherwise, $R_{51}$, $R_{52}$, $R_{53}$, $R_{54}$, $R_{55}$, $R_{56}$, $R_{57}$, $R_{59}$, $R_{60}$, $R_{61}$, $R_{62}$, or $R_{63}$ have a total carbon atom number of not more than 15; when the couplers are of a bis form, a telomer form, or a polymer form, any of $R_{51}$, $R_{52}$, $R_{53}$, $R_{54}$, $R_{55}$, $R_{56}$, $R_{57}$, $R_{59}$, $R_{60}$, $R_{61}$, $R_{62}$, or $R_{63}$ groups represents a divalent group for linking a repeating unit and in this case, the total carbon atom number in each of $R_{51}$ to $R_{57}$ and $R_{59}$ to $R_{63}$ may be out of the above-mentioned range;

b represents 0 or 1;

$R_{52}$ and $R_{53}$ each represents an aromatic group or a heterocyclic group;

$R_{54}$ has the same meaning as $R_{41}$ or represents

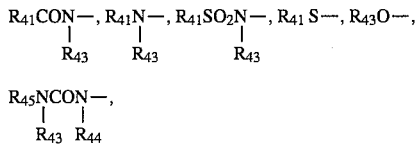

or $N\equiv C-$;

$R_{41}$ represents an aliphatic group, an aromatic group, or a heterocyclic group;

$R_{43}$, $R_{44}$, and $R_{45}$ each represent a hydrogen atom, an aliphatic group, an aromatic group, or a heterocyclic group;

$R_{51}$ and $R_{55}$ have the same meaning as $R_{41}$;

$R_{56}$ and $R_{57}$ each have the same meaning as $R_{43}$ or represent $R_{41}S-$, $R_{43}O-$,

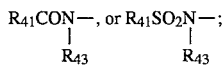

$R_{59}$ has the same meaning as $R_{41}$ or represents

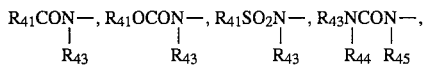

$R_{41}O-$, $R_{41}S-$, a halogen atom, or

d represents 0, 1, 2, or 3 and when d is 2 or 3, plural $R_{59}$'s may be the same or different, or each of them may represent a divalent group and be connected to each other to form a cyclic structure, $R_{60}$ has the same meaning as $R_{41}$;

$R_{61}$ has the same meaning as $R_{41}$;

$R_{62}$ has the same meaning as $R_{41}$ or represents $R_{41}OCONH-$, $R_{41}CONH-$, $R_{41}SO_2NH-$,

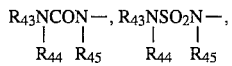

$R_{43}O-$, $R_{41}S-$, a halogen atom, or

$R_{63}$ has the same meaning as $R_{41}$ or represents

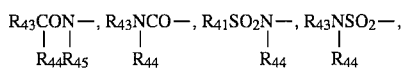

$R_{41}SO_2-$, $R_{43}OCO-$, $R_{43}OSO_2-$, $R_{41}CONH$, $R_{41}N(R_{43})SO_2-$, $R_{41}N(R_{43})CO-$, $R_{43}N(R_{43})CO-$, a halogen atom, a nitro group, a cyano group, or $R_{43}CO-$;

e represents 0 or an integer of from 1 to 4, and when e is 2 to 4, plural $R_{62}$ or $R_{63}$ may be the same or different.

15. The silver halide color photographic material as claimed in claim 14, wherein:

$R_{51}$ represents an aliphatic group or an aromatic group in formula (Cp-1) or a hydrogen atom or an aliphatic group in formula (Cp-2);

$R_{52}$, $R_{53}$, and $R_{55}$ each represent a heterocyclic group or an aromatic group;

$R_{54}$ represents $R_{41}CONH-$ or

$R_{56}$ and $R_{57}$ each represent an aliphatic group, an aromatic group, $R_{41}O-$, or $R_{41}S-$;

$R_{59}$ in formula (Cp-6) represents a chlorine atom, an aliphatic group, or $R_{41}CONH-$; and d represents 1 or 2;

$R_{59}$ in formula (Cp-7) represents $R_{41}CONH-$; and d represents 1;

$R_{60}$ represents an aromatic group;

$R_{61}$ represents an aliphatic group or an aromatic group;

e in formula (Cp-8) represents 0 or 1; and $R_{62}$ represents $R_{41}OCONH-$, $R_{41}CONH-$, or $R_{41}SO_2NH-$ and is bonded at the 5-position of the naphthol ring;

$R_{63}$ in formula (Cp-9) represents $R_{41}CONH-$, $R_{41}SO_2HN-$,

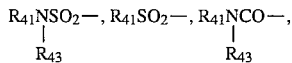

a nitro group, or a cyano group;

$R_{63}$ in formula (Cp-10) represents

$R_{43}OCO-$, or $R_{43}CO-$.

16. The silver halide color photographic material as claimed in claim 1, wherein the alkyl group is a straight chain or branched and substituted or unsubstituted alkyl group having from 1 to 4 carbon atoms.

17. The silver halide color photographic material as claimed in claim 1, wherein the total amount of the coupler of formula (I) is from $3\times10^{-7}$ to $1\times10^{-3}$ mol/m$^2$.

18. The silver halide color photographic material as claimed in claim 2, wherein the compounds represented by formula (A) are represented by formulae (B) or (C):

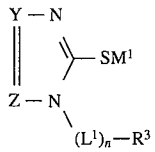

(B)

-continued

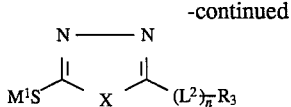
(C)

wherein in formula (B), Y and Z each represent a nitrogen atom or $CR^4$, wherein $R^4$ represents a hydrogen atom a substituted or unsubstituted alkyl group, or a substituted or unsubstituted aryl group; $R^3$ represents an organic residue, —$L^1$— represents a linking group selected from the group consisting of —S—, —O—,

—CO—, —SO—, and —$SO^2$—; n represents 0 or 1; and $M^1$, $M^2$, $R^1$, and $R^2$ are as defined above; and in formula (C), X represents a sulfur atom, an oxygen atom, or

$R^5$ represents a hydrogen atom, a substituted or unsubstituted alkyl group, or a substituted or unsubstituted aryl group; $L^2$ represents —$CONR^6$, —$NR^6CO$—, —$SO_2NR^6$, —$NR^6SO_2$—, —OCO—, —S—, —$NR^6$—, —CO—, —SO—, —OCOO—, —$NR^6CONR^7$—, —$NR^6COO$—, —$OCONR^6$—, or —$NR^6SO_2NR^7$—; $R^6$ and $R^7$ each represent a hydrogen atom, a substituted or unsubstituted alkyl group, or a substituted or unsubstituted aryl group; and $R^3$, $M^1$, $M^2$, are as defined above and n represents 0 or 1.

19. The silver halide color photographic material as claimed in claim 2, wherein the compound of formula (A) is present in an amount of from $1\times10^{-7}$ to $1\times10^{-3}$ mol/m$^2$.

* * * * *